(12) United States Patent
Liu

(10) Patent No.: US 9,023,957 B2
(45) Date of Patent: May 5, 2015

(54) COMPOUND FOR USE IN PEPTIDE SYNTHESIS

(75) Inventor: Chuan Fa Liu, Singapore (SG)

(73) Assignee: Nanyang Technological University, Singapore (SG)

( * ) Notice: Subject to any disclaimer, the term of this patent is extended or adjusted under 35 U.S.C. 154(b) by 167 days.

(21) Appl. No.: 13/808,303

(22) PCT Filed: Jul. 6, 2011

(86) PCT No.: PCT/SG2011/000236
§ 371 (c)(1),
(2), (4) Date: Feb. 5, 2013

(87) PCT Pub. No.: WO2012/005691
PCT Pub. Date: Jan. 12, 2012

(65) Prior Publication Data
US 2013/0131286 A1    May 23, 2013

(30) Foreign Application Priority Data
Jul. 6, 2010    (SG) .................. 201004859-3

(51) Int. Cl.
*C07K 1/107*   (2006.01)
*C07K 1/04*    (2006.01)
*C07C 323/29*  (2006.01)
*C07K 1/08*    (2006.01)

(52) U.S. Cl.
CPC ............ *C07K 1/1077* (2013.01); *C07C 323/29* (2013.01); *C07K 1/04* (2013.01); *C07K 1/086* (2013.01)

(58) Field of Classification Search
CPC ........ C07K 1/003; C07K 1/00; C07K 1/1075; C07K 1/107; C07K 1/067; C07K 1/061; C07K 1/06; C07K 1/062; C07K 7/00
See application file for complete search history.

(56) References Cited

FOREIGN PATENT DOCUMENTS

| WO | WO-02/098902 A2 | 12/2002 | |
| WO | WO/2005/092391 | * 6/2005 | .............. A61K 47/48 |
| WO | WO-2005/092391 A2 | 10/2005 | |
| WO | WO-2011/011342 A1 | 1/2011 | |
| WO | WO-2011/051906 A1 | 5/2011 | |

OTHER PUBLICATIONS

Nakamura et al., Bull. Chem. Soc. Jpn. (2006) 79(11), 1773-1780.*
Zhang et al., Tetrahedron Letters (2008) 49, 6122-6125.*
(Millipore # 856087 Cysteamine 4-methoxytrityl resin retrieved from http://www.emdmillipore.com/life-science-research/cysteamine-4-methoxytrityl-resin/EMD_BIO-856087/p_p4ib.s1OQIoAAAEjnBI9.zLX.*
Hackenberger et al., Angew. Chem. Int. Ed. (2008) 47, 10030-10074.*
Groth et al., New Linked Macrocyclic Systems Derives From Selectively Protected S2N2 Macrocycles, Journal of the Chemical Society, Perkin Transactions 1: Organic and Bio Organic Chemistry, 13: 1553-1558 (1996).
International Search Report of PCT/SG11/00236, dated Sep. 27, 2011 (11 pages).
Written Opinion of PCT/SG11/00236, dated Sep. 27, 2011 (10 pages).

* cited by examiner

*Primary Examiner* — Karlheinz R Skowronek
*Assistant Examiner* — Catherine Mader
(74) *Attorney, Agent, or Firm* — Choate, Hall & Stewart LLP; Charles E. Lyon; Kevin M. Henry

(57) ABSTRACT

The present invention generally relates to processes and methods of peptide and protein synthesis. The present invention also relates to specific compounds for use in such processes and methods. It is shown herein that peptides with a C-terminal tertiary N,N-bis(2-mercaptoethyl)-amide (BMEA) undergo N-to-S acyl transfer at weakly acidic pH to form a transient thioester which can be captured for direct ligation with a cysteinyl peptide. These C-terminal BMEA peptides are easily prepared with standard Fmoc solid-phase synthesis protocols, thus giving a very convenient access to the thioester components for native chemical ligation.

26 Claims, 26 Drawing Sheets

A

B

Figure 12 contd.
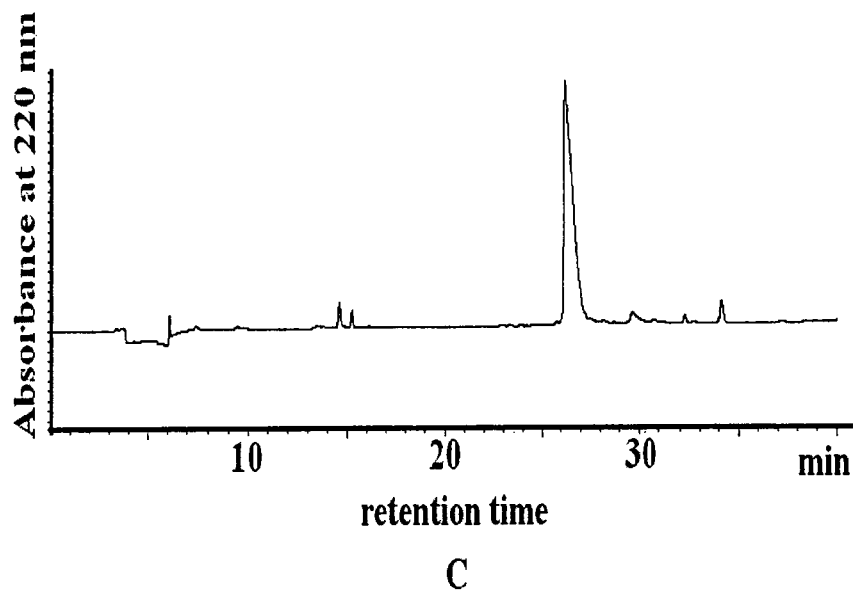
C
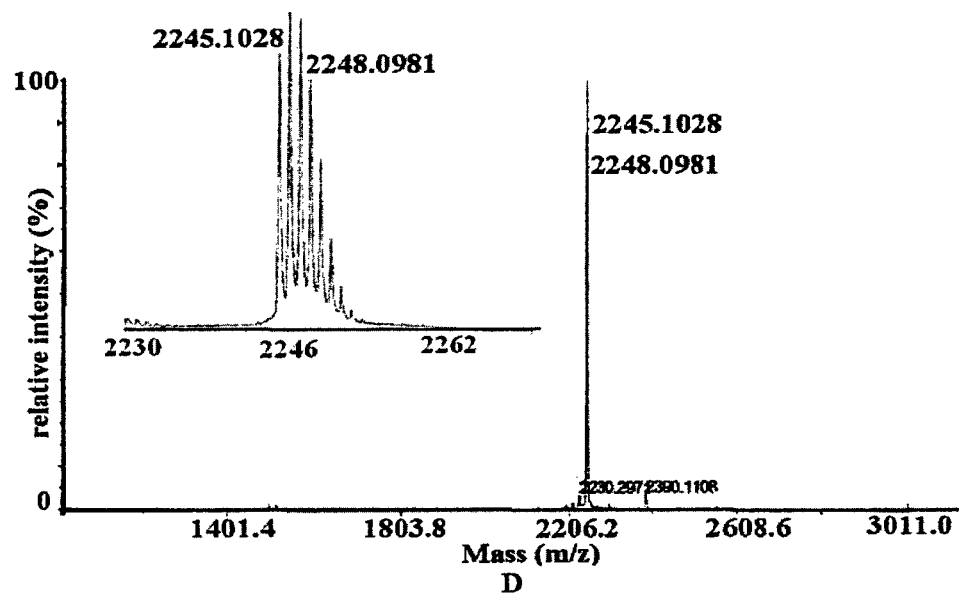
D

Figure 19 contd.
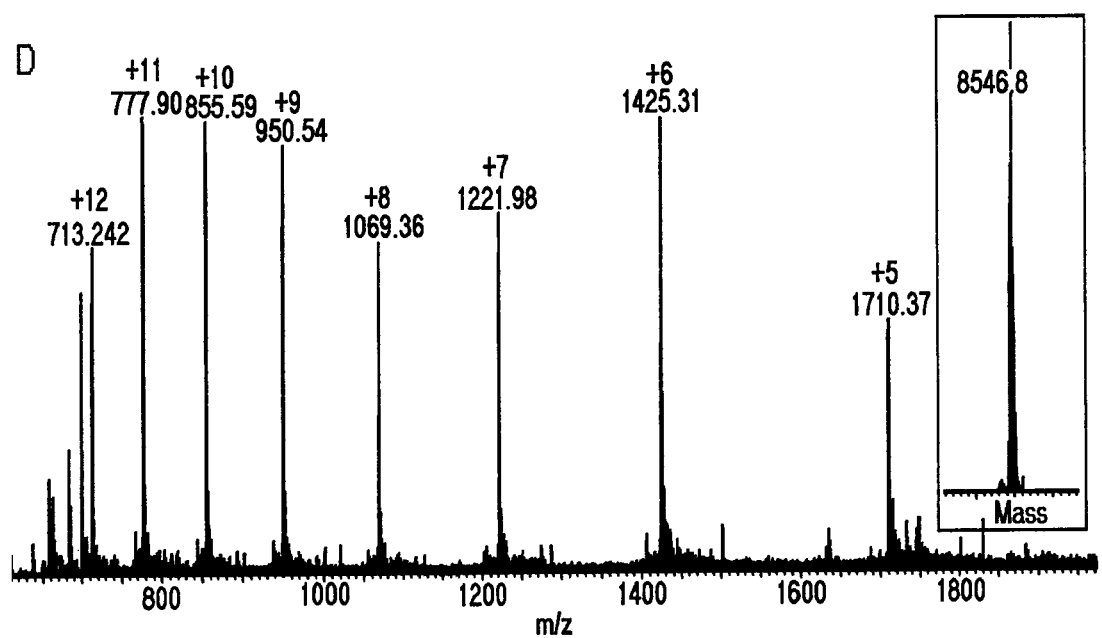

A  B  C

SEQUENCE LISTING

<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: synthetic sequence

```
<220> FEATURE:
<221> NAME/KEY: MOD_RES
<222> LOCATION: (5)..(5)
<223> OTHER INFORMATION: Where position 5 is modied with (CH2CH2SH)2

<400> SEQUENCE: 1

Leu Lys Ser Phe Gly
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic sequence

<400> SEQUENCE: 2

Cys Leu Lys Phe Ala
1               5

<210> SEQ ID NO 3
<211> LENGTH: 5
<212> TYPE: PRT
<213> ORGANISM: Artificial Sequence
<220> FEATURE:
<223> OTHER INFORMATION: synthtic sequence
<220> FEATURE:
<221> NAME/KEY: MOD_RES
<222> LOCATION: (5)..(5)
<223> OTHER INFORMATION: Where position 5 is modifed with MESN.

<400> SEQUENCE: 3

Leu Lys Ser Phe Gly
1               5

<210> SEQ ID NO 4
<211> LENGTH: 18
<212> TYPE: PRT
<213> ORGANISM: Artificial Sequence
<220> FEATURE:
<223> OTHER INFORMATION: synthtic sequence
<220> FEATURE:
<221> NAME/KEY: MOD_RES
<222> LOCATION: (18)..(18)
<223> OTHER INFORMATION: Wherein position 18 is modified with
      -S(CH2)2CONH2

<400> SEQUENCE: 4

Ala Asp Lys Arg Ala His His Asn Ala Leu Glu Arg Lys Arg Arg Asp
1               5                   10                  15

His Ala

<210> SEQ ID NO 5
<211> LENGTH: 11
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (11)..(11)
<223> OTHER INFORMATION: Wherein position 11 is modified with
      -N(CH2CH2SH)2

<400> SEQUENCE: 5

Cys Asp Ser Phe His Ser Leu Arg Asp Ser Tyr
1               5                   10
```

```
<210> SEQ ID NO 6
<211> LENGTH: 17
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (12)..(12)
<223> OTHER INFORMATION: PHOSPHORYLATION

<400> SEQUENCE: 6

Cys Leu Lys Pro Leu His Glu Lys Asp Ser Glu Ser Gly Gly Gly Lys
1               5                   10                  15

Asp

<210> SEQ ID NO 7
<211> LENGTH: 29
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (29)..(29)
<223> OTHER INFORMATION: Wherein position 29 is modified with
      -N(CH2CH2SH)2

<400> SEQUENCE: 7

Ala Asp Lys Arg Ala His His Asn Ala Leu Glu Arg Lys Arg Arg Asp
1               5                   10                  15

His Ala Cys Asp Ser Phe His Ser Leu Arg Asp Ser Tyr
            20                  25

<210> SEQ ID NO 8
<211> LENGTH: 46
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (41)..(41)
<223> OTHER INFORMATION: PHOSPHORYLATION

<400> SEQUENCE: 8

Ala Asp Lys Arg Ala His His Asn Ala Leu Glu Arg Lys Arg Arg Asp
1               5                   10                  15

His Ala Cys Asp Ser Phe His Ser Leu Arg Asp Ser Tyr Cys Leu Lys
            20                  25                  30

Pro Leu His Glu Lys Asp Ser Glu Ser Gly Gly Gly Lys Asp
        35                  40                  45

<210> SEQ ID NO 9
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (5)..(5)
<223> OTHER INFORMATION: Where position 5 is modified with (NCH2CH2SH,
      CH2CH2CH2SH)

<400> SEQUENCE: 9

Leu Lys Ser Phe Gly
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (5)..(5)
<223> OTHER INFORMATION: Where position 5 is modied with N(CH2CH2CH2SH)2

<400> SEQUENCE: 10

Leu Lys Ser Phe Gly
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (5)..(5)
<223> OTHER INFORMATION: Where position 5 is modified with
      (NCH2CH2CH2SH)2

<400> SEQUENCE: 11

Leu Lys Ser Phe Gly
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (5)..(5)
<223> OTHER INFORMATION: Where position 5 is modified with N(CH2CH2SH,
      CH2CH2CH2SH)

<400> SEQUENCE: 12

Leu Lys Ser Phe Gly
1               5

<210> SEQ ID NO 13
<211> LENGTH: 33
<212> TYPE: DNA
<213> ORGANISM: Artificial Sequence
<220> FEATURE:
<223> OTHER INFORMATION: synthetic sequence

<400> SEQUENCE: 13
gaggacacca acctggccgc catccacgcc aag                                33

<210> SEQ ID NO 14
<211> LENGTH: 33
<212> TYPE: DNA
<213> ORGANISM: Artificial Sequence
<220> FEATURE:
<223> OTHER INFORMATION: synthetic sequence

<400> SEQUENCE: 14
cttggcgtgg atggcggcca ggttggtgtc ctc                                33
```

```
<210> SEQ ID NO 15
<211> LENGTH: 51
<212> TYPE: DNA
<213> ORGANISM: Artificial Sequence
<220> FEATURE:
<223> OTHER INFORMATION: synthetic sequence

<400> SEQUENCE: 15
ctttaagaag gagatataca tatgtgcgct ccccgcaagc agctggccac c          51

<210> SEQ ID NO 16
<211> LENGTH: 51
<212> TYPE: DNA
<213> ORGANISM: Artificial Sequence
<220> FEATURE:
<223> OTHER INFORMATION: synthetic sequence

<400> SEQUENCE: 16
ggtggccagc tgcttgcggg gagcgcacat atgtatatct aattcttaaa g          51

<210> SEQ ID NO 17
<211> LENGTH: 27
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (27)..(27)
<223> OTHER INFORMATION: Wherein position 27 is modified with
      -S(CH2)2CONH2

<400> SEQUENCE: 17

Leu Gln Ile Phe Val Lys Thr Leu Thr Gly Lys Thr Ile Thr Leu Glu
1               5                   10                  15

Val Glu Pro Ser Asp Thr Ile Glu Asn Val Lys
            20                  25

<210> SEQ ID NO 18
<211> LENGTH: 18
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (18)..(18)
<223> OTHER INFORMATION: Wherein position 18 is modified with
      -N(CH2CH2SH)2

<400> SEQUENCE: 18

Cys Asp Ile Gln Asp Lys Glu Gly Ile Pro Pro Asp Gln Gln Arg Leu
1               5                   10                  15

Ile Phe

<210> SEQ ID NO 19
<211> LENGTH: 31
<212> TYPE: PRT
<213> ORGANISM: Artificial Sequence
<220> FEATURE:
<223> OTHER INFORMATION: synthetic sequence

<400> SEQUENCE: 19

Cys Gly Lys Gln Leu Glu Asp Gly Arg Thr Leu Ser Asp Tyr Asn Ile
1               5                   10                  15

Gln Lys Glu Ser Thr Leu His Leu Val Leu Arg Leu Arg Gly Gly
            20                  25                  30
```

```
<210> SEQ ID NO 20
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (5)..(5)
<223> OTHER INFORMATION: Where position 5 is modified with
      SCH2CH2NHCH2CH2CH2SH

<400> SEQUENCE: 20

Leu Lys Ser Phe Gly
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (5)..(5)
<223> OTHER INFORMATION: Where position 5 is modieid with
      SCH2CH2CH2NHCH2CH2SH

<400> SEQUENCE: 21

Leu Lys Ser Phe Gly
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic sequence

<400> SEQUENCE: 22

Leu Lys Ser Phe Gly
1               5
```

COMPOUND FOR USE IN PEPTIDE SYNTHESIS

REFERENCE TO SEQUENCE LISTING

The specification includes a Sequence Listing in the form of an ASCII compliant text file named "Sequence Listing.txt", which was created on Mar. 21, 2014 and has a size of 6.53 kilobytes. The content of the aforementioned "Sequence Listing.txt" file is hereby incorporated by reference in its entirety.

TECHNICAL FIELD

The present invention generally relates to processes and methods of peptide and protein synthesis. The present invention also relates to specific compounds for use in such processes and methods. It is shown herein that peptides with a C-terminal tertiary N,N-bis(2-mercaptoethyl)-amide (BMEA) undergo N-to-S acyl transfer at weakly acidic pH to form a transient thioester which can be captured for direct ligation with a cysteinyl peptide. These C-terminal BMEA peptides are easily prepared with standard Fmoc solid-phase synthesis protocols, thus giving a very convenient access to the thioester components for native chemical ligation.

INTRODUCTION

Peptide $C^\alpha$-thioesters have been increasingly used as key building blocks for a number of protein synthesis strategies[1] including, notably, native chemical ligation.[2] The highly successful native chemical ligation scheme utilizes a peptide thioester to ligate with another peptide containing an N-terminal cysteine residue. This has stimulated significant interest in developing new and convenient methods to prepare these important compounds in recent years.[3] Traditionally, thioester peptides are prepared with the Boc solid phase synthesis method whereby the peptide chain is assembled directly on a thioester linker.[1a,4] Although this method is very effective, the need for a highly hazardous strong acid such as HF at the final cleavage step represents a deterring element to many research laboratories. Direct Fmoc-solid phase synthesis of peptide thioesters on a thioester linker is also possible using a modified Fmoc-deprotection protocol, but its use is restricted to relatively small peptides and racemization of the C-terminal amino acid residue is a significant problem.[5] Considerable efforts have been devoted to developing alternative strategies to obtain thioester peptides indirectly from non-thioester precursors the synthesis of which is compatible with standard Fmoc chemistry.[6-8] For example, certain activated amide systems based on Kenner's safety-catch sulfonamides,[6a,b,c] acylureas[6d] and pyroglutamyl imides[6e] have been developed. Other systems utilize N→S acyl transfer to produce thioesters,[9,10] which in a way are mechanistically reminiscent of protein splicing.[11] Many of these systems require acidic conditions to catalyze amide-to-thioester conversion which is followed by transthioesterification with a free thiol compound to generate a thioester. Aimoto's group reported the use of an autoactivating C-terminal Cys-Pro ester (CPE) to mediate amide-to-thioester conversion at neutral or slightly basic pH as it is driven by diketopiperazine formation to trap the transiently exposed alpha-amine of Cys through intramolecular aminolysis of the prolyl ester.[10a] Despite an inconvenience in loading the 1st amino acid to the CPE linker and the need for a relatively reactive glycolic ester at the C-terminus, this method is appealing for its clever design.

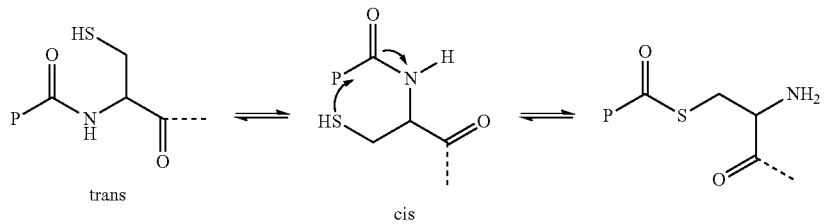

Scheme 1. N→S acyl transfer involving a peptidyl-Cys amide bond.

In our efforts to develop new and convenient methods for peptide thioester synthesis, we have paid particular attention to the N→S acyl transfer reaction. Mechanistically, it is recognized that, in order for the N→S acyl transfer to take place, the planar amide bond must be in the configuration where the thiol-bearing N-substituent is anti to the carbonyl oxygen. This requires an energetically unfavorable cis isomer of the 2° amide in a regular Xaa-Cys peptide bond (Scheme 1). And to drive the reaction equilibrium towards thioester formation, there must be a trapping mechanism, e.g., protonation, for the newly exposed amine. In protein splicing, trans-cis amide isomerization is presumably catalyzed by the intein which also serves as a general acid-base catalyst for thioesterification.[11] $N^\alpha$-Cys alkylation such as methylation or ethylation is also known to facilitate trans-cis isomerization of the Xaa-Cys amide bond and the use of acidic conditions would then promote N→S acyl migration.[9d] These rationales have led us to propose a new N→S acyl transfer system to generate thioesters for NCL, as shown in Scheme 2. This reaction system is based on the use of a peptide C-terminal tertiary amide 1, namely N,N-bis(2-mercaptoethy)-amide or BMEA. With two β-mercaptoethyl (HS-Et) N-substitutions, this amide will always have one HS-Et group correctly positioned for the intramolecular thiolysis reaction. And the relative strong basicity of the $2^{nd}$ amine in the thioesterification product 2 would make its trapping easier by protonation, which might allow shifting the N→S acyl transfer reaction equilibrium to a useful extent at NCL-operable pH. Coupling thioesterification with native chemical ligation would then ultimately lead the overall reaction to its forward direction (Scheme 2).

Scheme 2. N-to-S acyl transfer using an N,N-di-(2-mercaptoethyl)-substituted tertiary amide to generate thioester peptides for NCL.

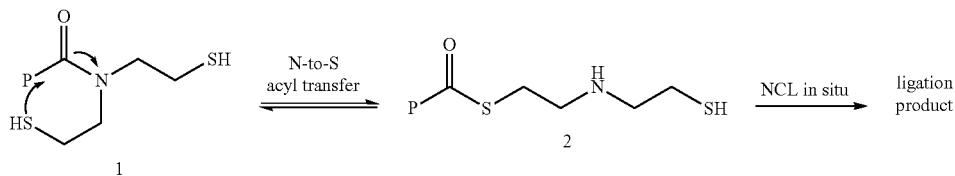

SUMMARY

Peptide thioesters are essential building blocks for protein synthesis. The technology we have developed provides easy access to peptide thioesters which are convenient to prepare by Fmoc solid phase peptide synthesis and are also relatively efficient for use in NCL with a cysteinyl-peptide.

Our design is based on a C-terminal tertiary amide, namely N,N-bis(2-mercaptoethy)-amide or BMEA of which the nitrogen is substituted with two beta-mercaptoethyl or HS-et groups.

The presence of two such HS-Et N-substitutions makes this amide always ready to undergo an intramolecular thiolysis reaction (i.e. N→S acyl transfer) to convert itself to a thioester. Once formed, the thioester product can be used directly for NCL with a cysteinyl peptide, leading to formation of the ligation. In contrast, other thioester precursors do not allow both thioester and thio-thioester exchange to occur in one step and require the additional step of generating the thioester before NCL can proceed.

We have also devised a straightforward method for preparing the BMEA linker-derived resin onto which a peptide chain can be assembled easily using standard Fmoc solid phase peptide synthesis protocols. Model studies with a panel of selected BMEA peptides have validated our hypothesis and demonstrated the scope of these peptides for NCL as well as their utility in protein synthesis (e.g. histone H3 synthesis).

These and other aspects of the invention will be apparent from the more detailed description of the invention below and the Examples section of this specification.

It should be understood that whilst various references are made herein to BMEA/BMEA moieties, the invention is not limited to such moieties and, as such, references herein to BMEA/BMEA moieties apply mutatis mutandis to variants of BMEA/BMEA moieties as taught herein, unless the context indicates otherwise. In this regard, we have demonstrated that variants of BMEA work in which one N-substitution is 2-mercaptoethyl and one is 3-mercaptopropyl (see Example 4). Further, the teachings herein in relation to BMEA/BMEA moieties may be modified by the use of a cysteine in place of a mercaptoethylamine of the BMEA. Thus, the teachings herein in relation to BMEA/BMEA moieties extend to these and other variants.

The sequential ligation was performed through the combination of thioester mediated native chemical ligation and peptidyl N,N-bis(2-mercaptoethyl)-amide mediated ligation. The approach has been successfully applied to the chemical synthesis of ubiquitin and therefore the potential usefulness of the approach in protein synthesis has been demonstrated.

Figure 8:
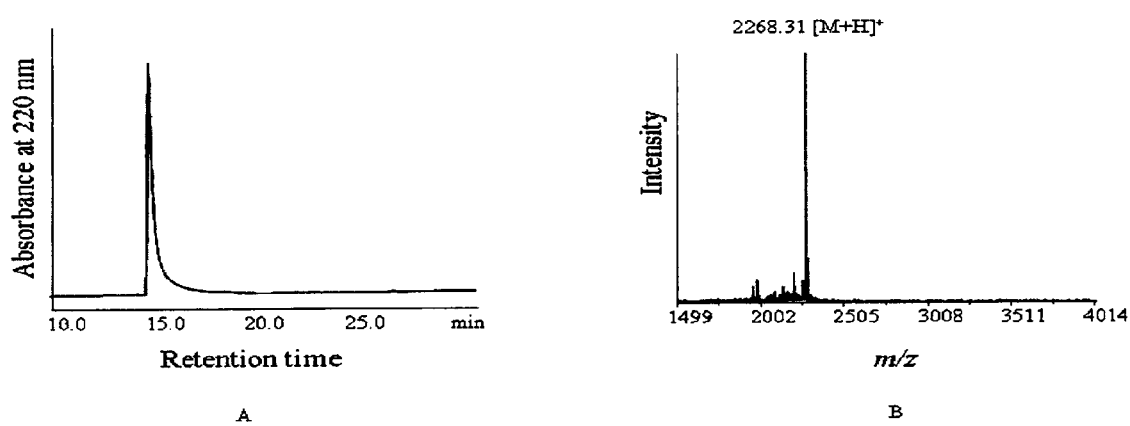

FIG. 8 C18 analytic HPLC profile (A) and MALDI-TOF MS spectrum (B) of peptide 1, H-ADKRAHH-NALERKRRDHA-SCH$_2$CH$_2$CONH$_2$ (SEQ ID NO:4). HPLC gradient: 0% to 40% of buffer B in buffer A in 40 min. [M+H]$^+$ found: 2268.31, isotopic MW calculated: 2267.17 Da.

Figure 9:
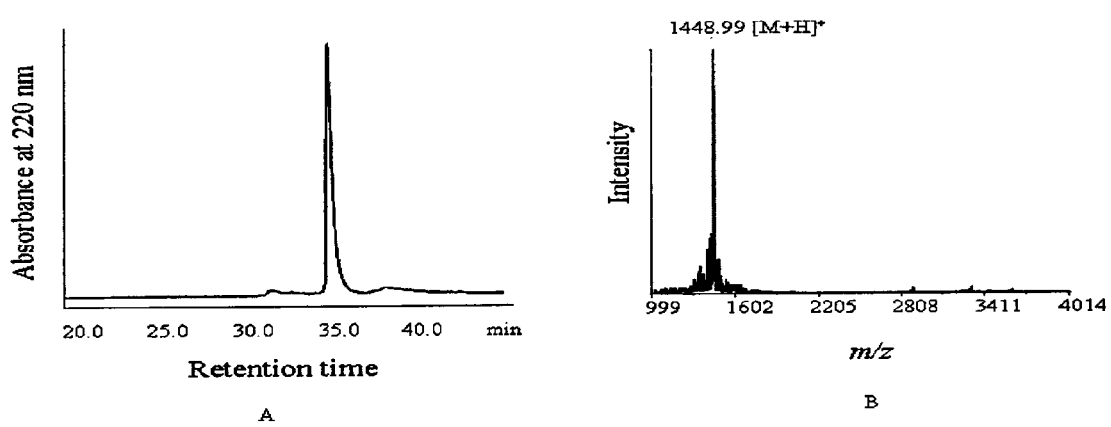

FIG. 9 C18 analytic HPLC profile (A) and MALDI-TOF MS spectrum (B) of peptide 2, H-CDSFHSLRDSY-N(CH$_2$CH$_2$SH)$_2$ (SEQ ID NO:5). HPLC gradient: 0% to 40% of buffer B in buffer A in 40 min [M+H]$^+$ found: 1448.99, isotopic MW calculated: 1447.57 Da.

Figure 10:
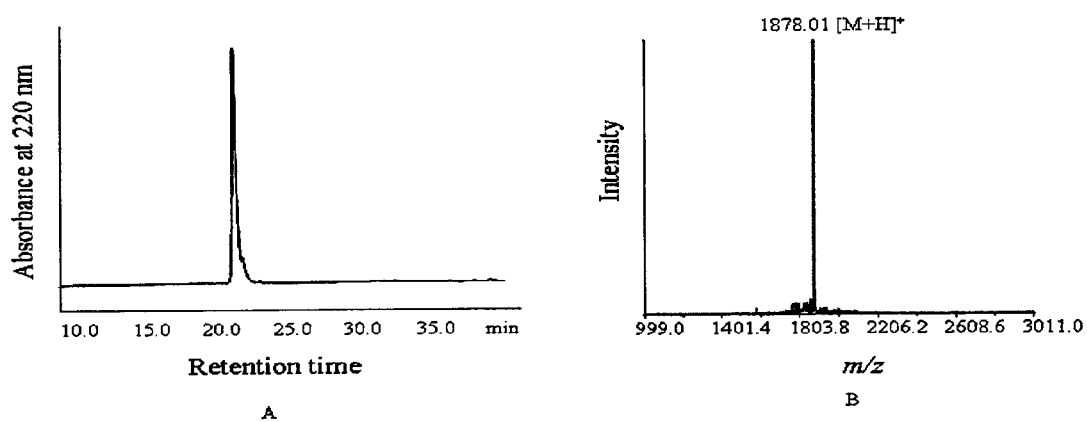

FIG. 10 C18 analytic HPLC profile (A) and MALDI-TOF MS spectrum (B) of peptide 3, H-CLKPLHEKDSES$_{(P)}$GGGKD-NH$_2$ (SEQ ID NO:6). HPLC gradient: 0% to 40% of buffer B in buffer A in 40 min [M+H]$^+$ found: 1878.01; isotopic MW calculated: 1876.83 da.

Figure 11:
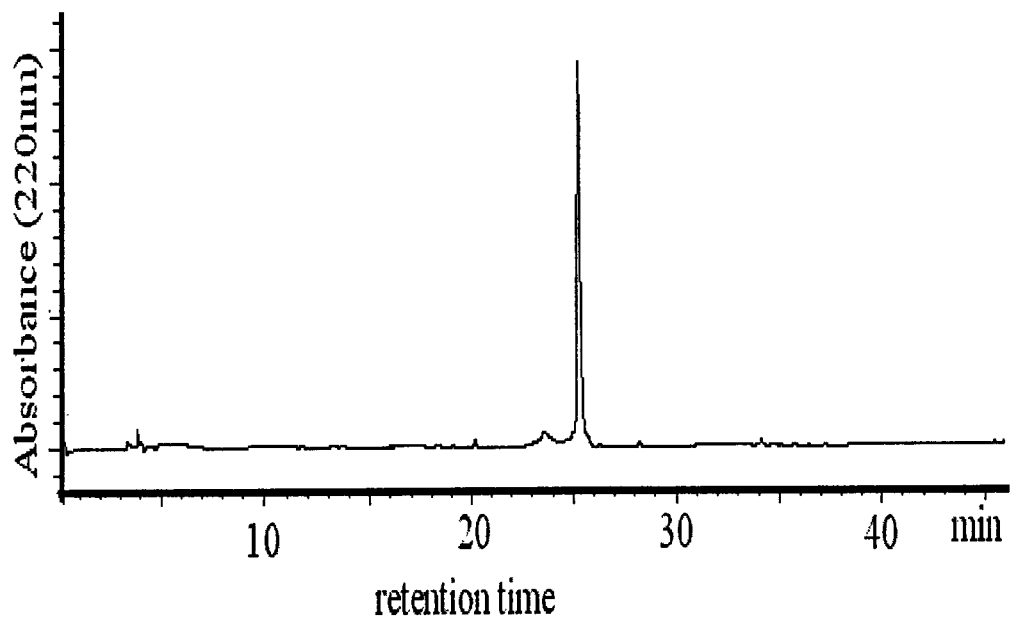
Figure 11:
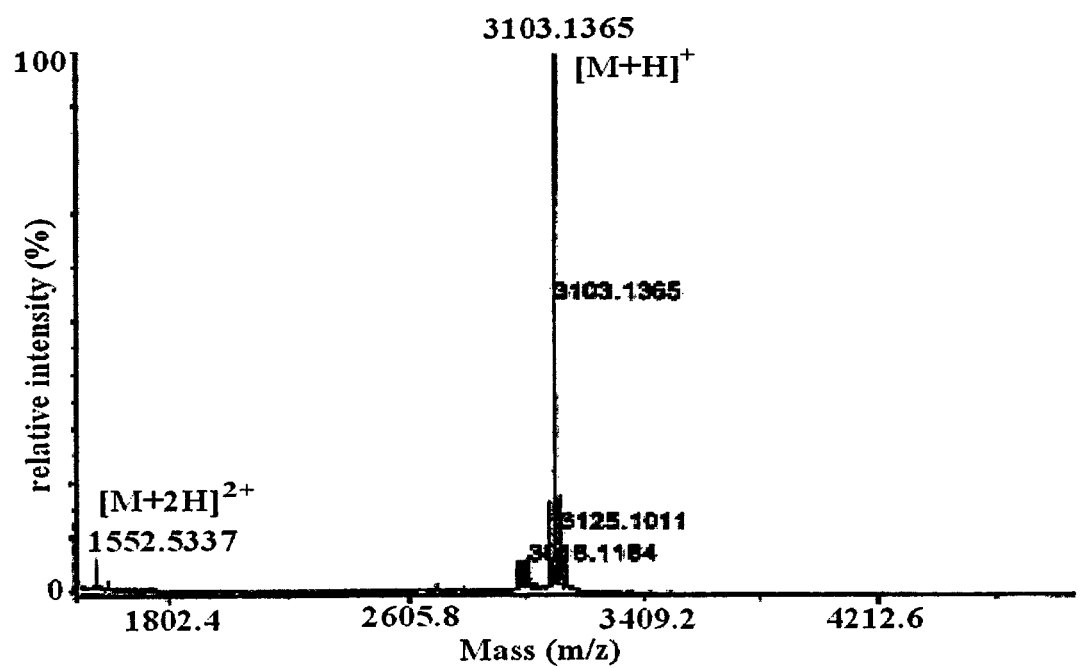

FIG. 11 C18 analytic HPLC profile (top) and MALDI-TOF MS spectrum (bottom) of peptide 4, Ubi H-LK$_{27}$-SCH$_2$CH$_2$CONH$_2$. HPLC condition: 0% to 80% of buffer B in buffer A in 40 min. [M+H]$^+$ found: 3103.1365; isotopic MW calcd: 3102.69 Da.

Figure 12:
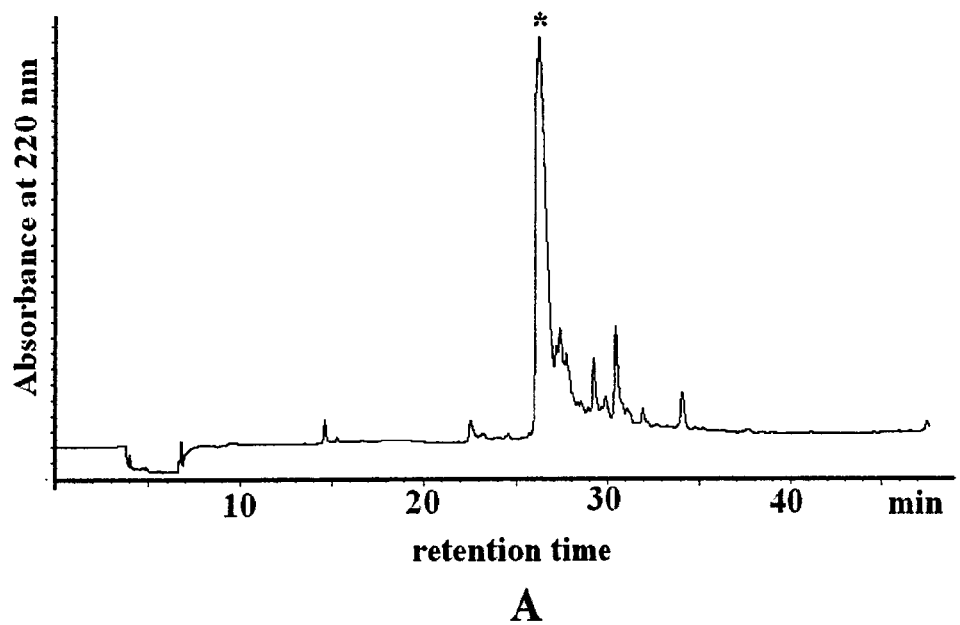
Figure 12:
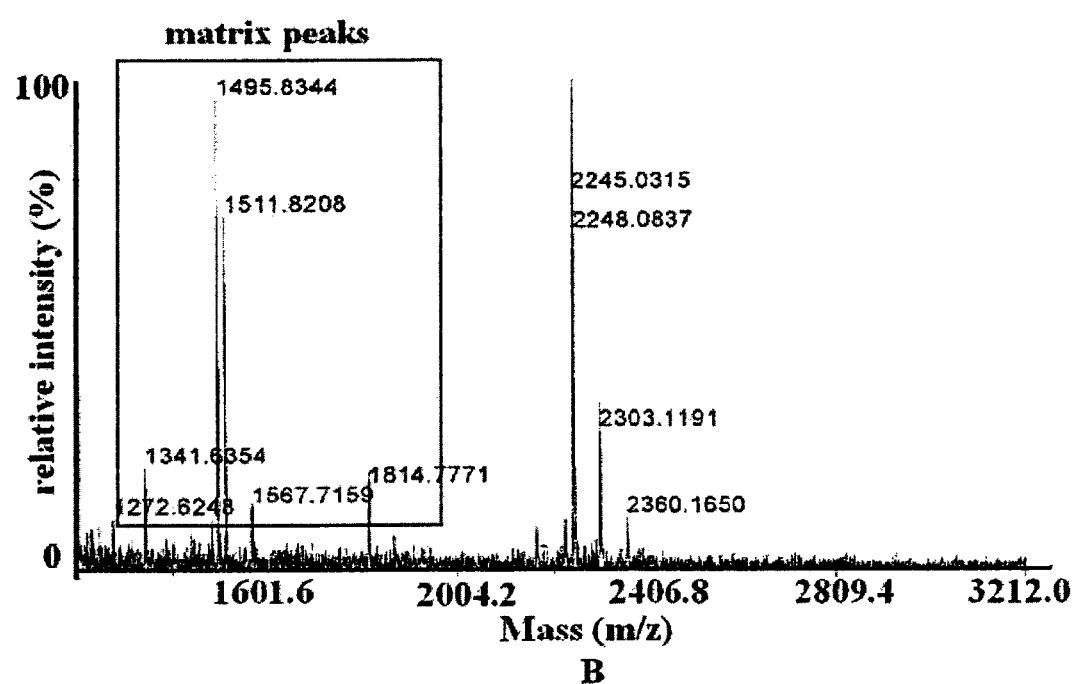

FIGS. 12 A) and B): C18 analytic HPLC profile (A) and MALDI-TOF MS spectrum (B) of the crude peptide 5, ubi H-C$_{28}$-F$_{45}$-BMEA synthesized using the revised strategy. The asterisked peak in Fig. A is the desired product containing 5 as well as its BMEA oxidized form (disulfide form). The peaks highlighted with rectangle in Fig B are matrix peaks. The peak with mass 2245.0315 and 2248.0981 is the oxidized and reduced form of 5, respectively. Peaks 2303.1191 and 2360.1650 are S-alkylated products with addition of one t-butyl and two t-butyl groups, respectively.

C) and D): C18 analytic HPLC profile (C) and MALDI-TOF MS spectrum (D) of the purified 5. HPLC gradient: 0% to 80% of buffer B in buffer A in 40 min [M+H]$^+$ found: 2245.10 (oxidized) and 2248.10 (reduced). The calculated isotopic MW of the oxidized form is 2244.12 Da, reduced form 2246.14 Da.

Figure 13:
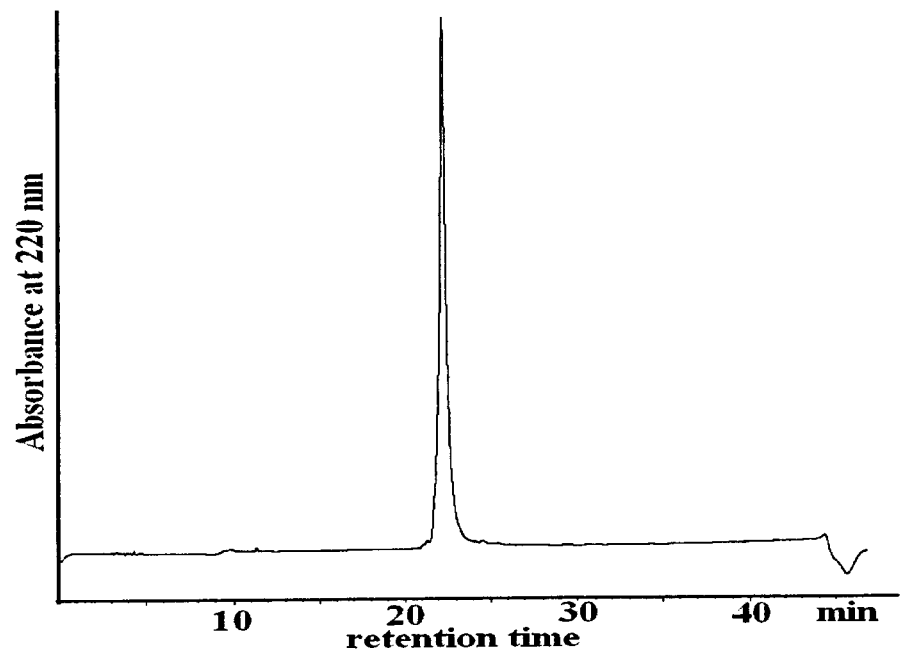
Figure 13:
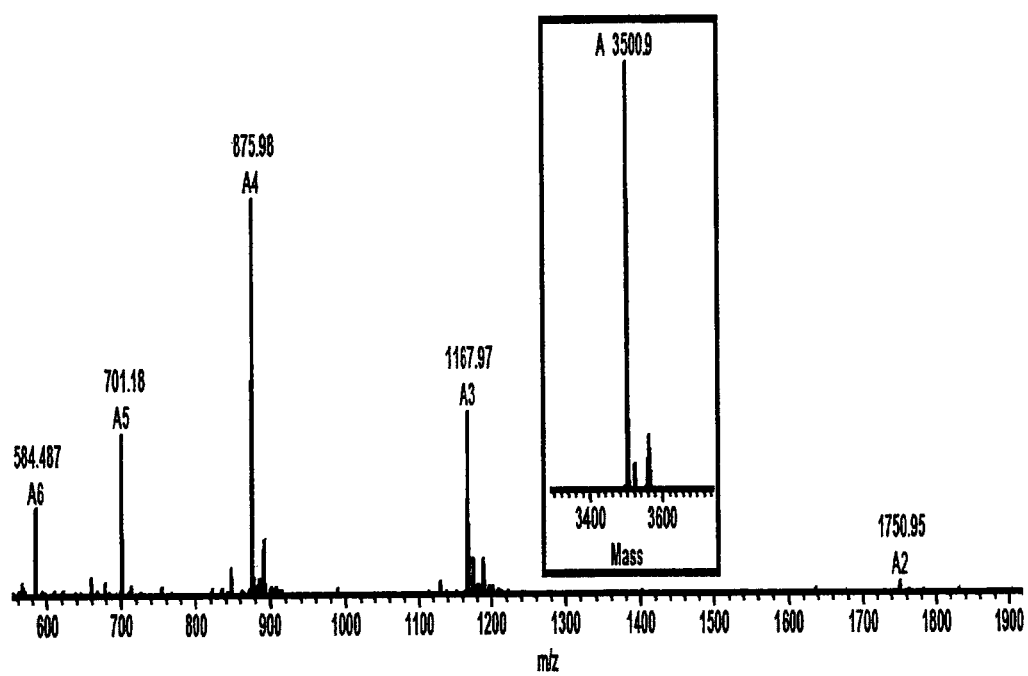

FIG. 13 C18 analytic HPLC profile (top) and ESI-MS spectrum (bottom) of peptide 6, Ubi H-C$_{46}$-G$_{76}$-OH. HPLC gradient: 0% to 80% of buffer B in buffer A in 40 min. MW found: 3500.9, MW calcd: 3500.94 Da.

Figure 14:
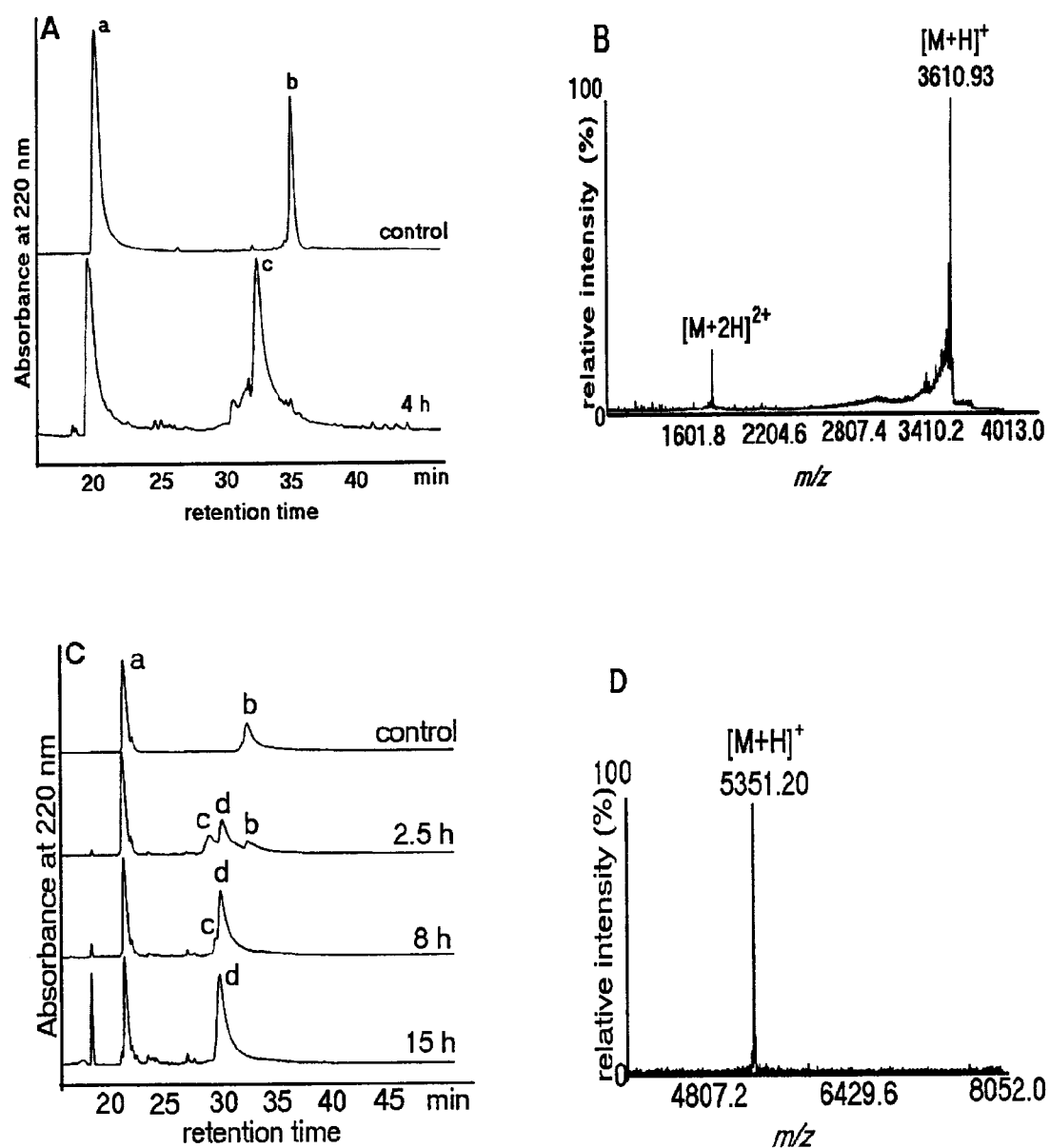

FIG. 14 The study of the N to C sequential ligation strategy with model peptides. A): C18 analytical HPLC analysis of the ligation reaction between peptide 1 and 2. HPLC condition: 0% to 40% of buffer B in buffer A in 40 min Peak a: peptide 1; peak b: peptide 2; peak c: ligation product of 1 and 2, H-ADKRAHHNALERKRRDHACDSFHSLRDSY-N (CH$_2$CH$_2$SH)$_2$ (SEQ ID NO:7) or H-AY$_{29}$-BMEA. B): The MALDI-TOF MS of H-AY$_{29}$-BMEA. [M+H]$^+$ found: 3610.93, MW calcd: 3609.71. C): C18 analytical HPLC analysis of the ligation reaction between H-AY$_{29}$-BMEA and peptide 3. HPLC condition: 0% to 50% of buffer B in buffer A in 50 min. Peak a: peptide 3; peak b: H-AY$_{29}$-BMEA; peak c: H-AY$_{29}$-MES; peak d: ligation product, H-ADKRAHHNALERKRRDHA CDSFHSLRDSYCLK-PLHEKDSES($_p$)GGGKD-NH$_2$ (SEQ ID NO:8) or H-AD$_{46}$-NH$_2$. D): The MALDI-TOF MS of H-AD$_{46}$-NH$_2$. [M+H]$^+$ found: 5351.20, MW calcd: 5349.50.

Figure 15:
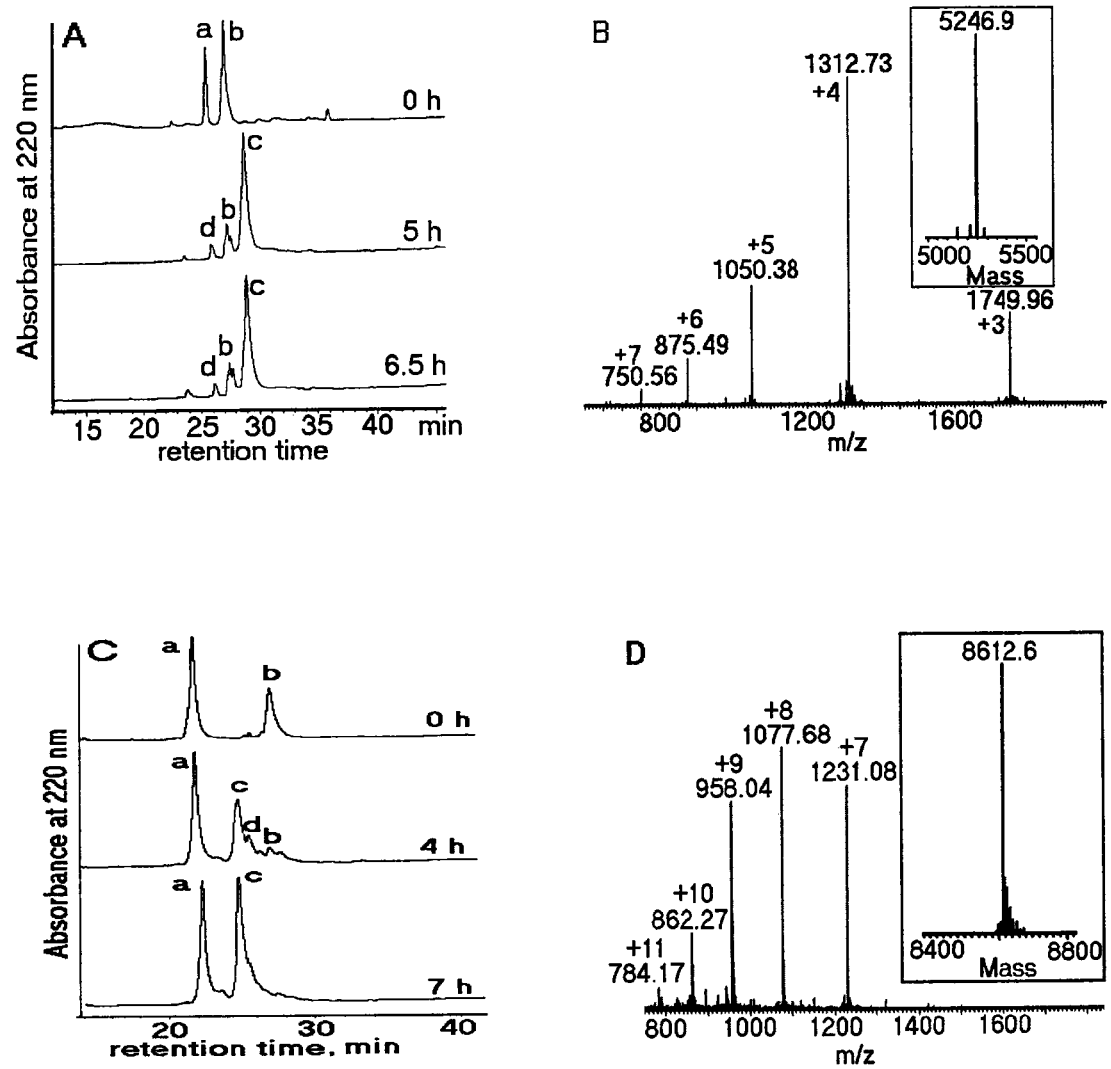

FIG. 15 The synthesis of ubiquitin using N to C sequential ligation. A): C18 analytical HPLC analysis of the ligation reaction between peptide 4 and 5. HPLC condition: 0% to 80% of buffer B in buffer A in 40 min. Peak a: peptide 4; peak b: peptide 5; peak c: ligation product of 4 and 5, H-LF$_{45}$-BMEA; peak d: self cyclization and hydrolysis product of 4. B): The raw and deconvoluted ESI-MS of H-LF$_{45}$-BMEA. MW found: 5246.9, MW calcd: 5247.16. C): C18 analytical HPLC analysis of the ligation reaction between H-LF$_{45}$-BMEA and peptide 6 with methyl mercaptoacetate as thiol additive. HPLC condition: 0% to 80% of buffer B in buffer A in 40 min. Peak a: peptide 6; peak b: H-LF$_{45}$-BMEA; peak c: ligation product; peak d: H-LF$_{45}$-SCH2COOMe. D): The raw and deconvoluted ESI MS of full length ubiquitin. MW found: 8612.6, MW calcd: 8610.8.

Figure 16:
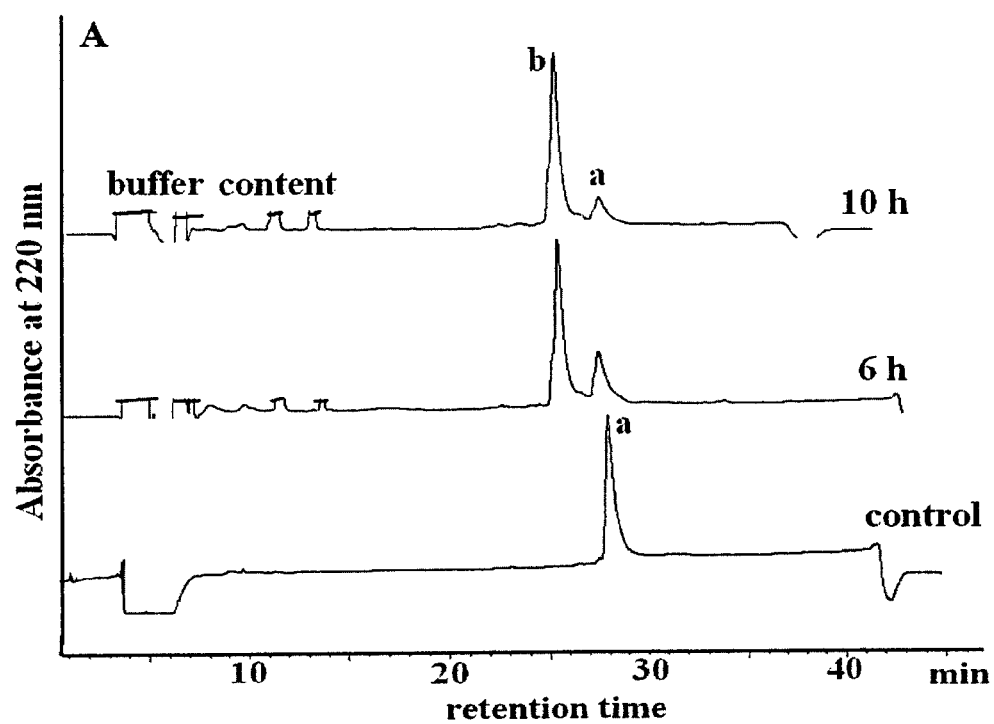
Figure 16:
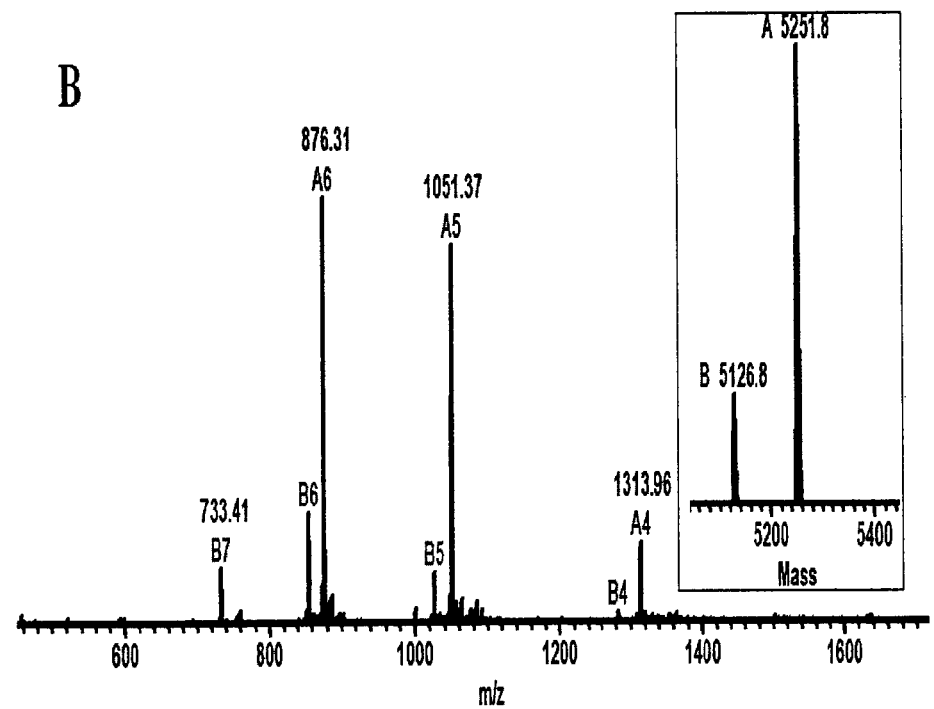

FIG. 16 The conversion of ubi H-LF$_{45}$-N(CH$_2$CH$_2$SH)$_2$ to ubi H-LF$_{45}$-MES through the exchange of BMEA moiety with MESNa under acidic and microwave condition. A): C18 analytic HPLC monitored reaction at 6 h and 10 h. Peak a: H-LF$_{45}$-N(CH$_2$CH$_2$SH)$_2$; Peak b: H-LF$_{45}$-MES with small amount of hydrolysis product, H-LF$_{45}$-OH. HPLC gradient: 0% to 80% of buffer B in buffer A for 40 min. B): The raw and deconvoluted ESI-MS of peak b. Species A: H-LF$_{45}$-MES, MW found 5251.8, calculated 5252.09; Species B: Ubi L1-F45-OH. MW found 5126.8, calculated 5127.91.

Figure 17:
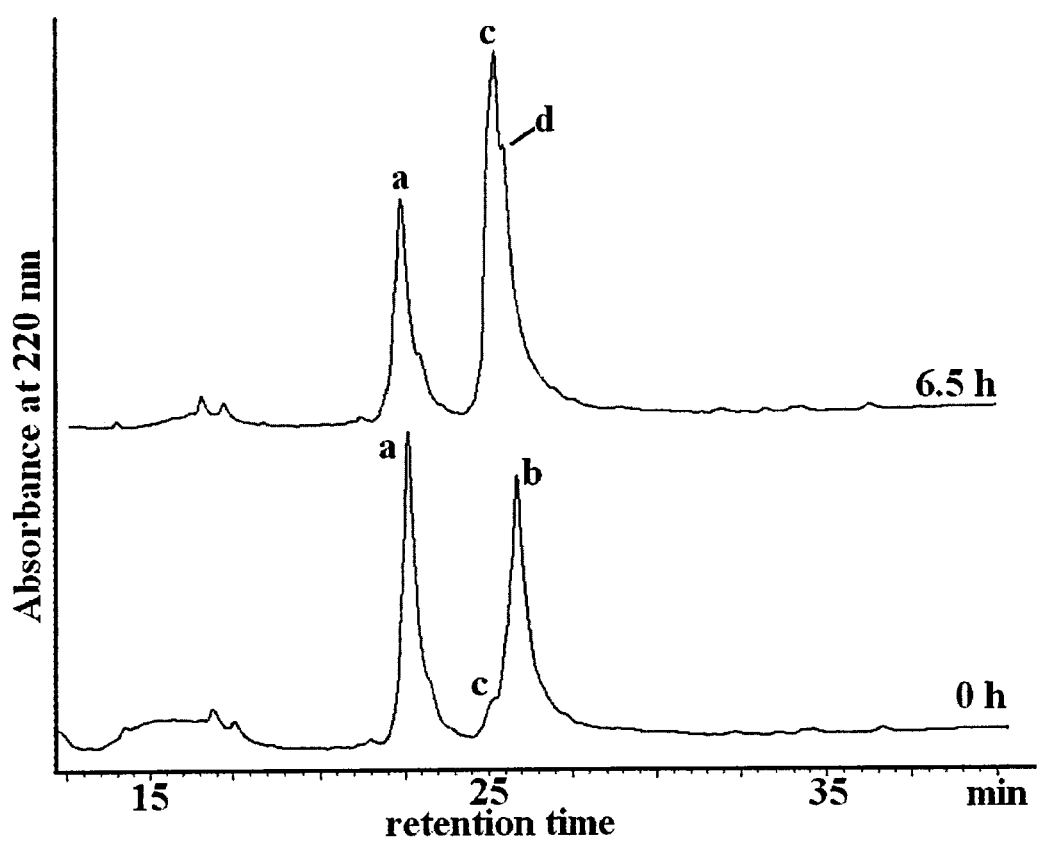

FIG. 17 C18 analytic HPLC monitored the ligation between isolated ubi L1-F45-MES with ubi C46-G-76-OH. Peak a: ubi C46-G-76-OH; Peak b: Ubi L1-F45-MES (containing small amount of Ubi L1-F45-OH); Peak c: ligation product, Ubi L1-G76-OG A28C, A46C; peak d: Ubi L1-F45-OH. HPLC gradient: 0% to 80% of buffer B in buffer A for 40 min.

Figure 18:
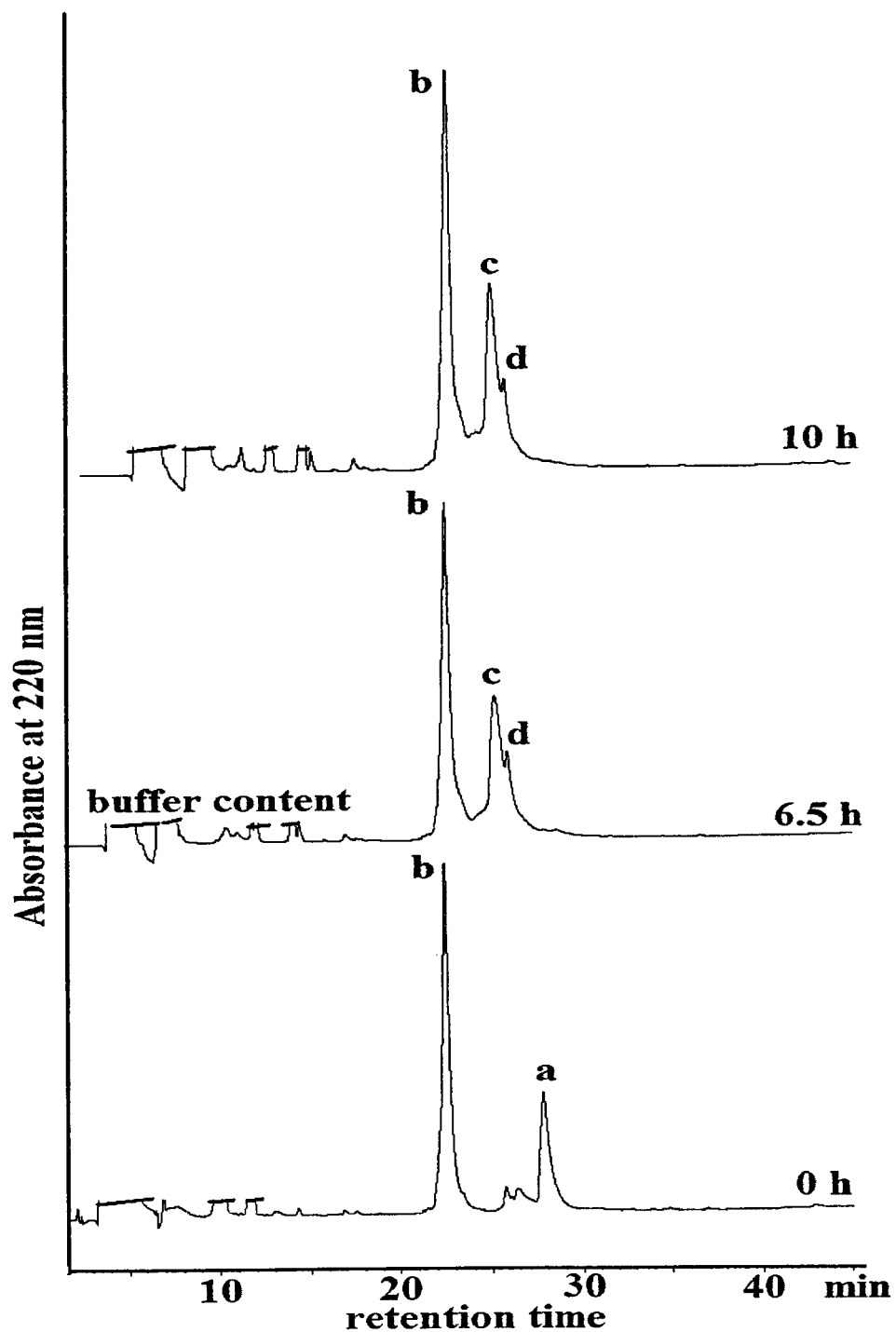

FIG. 18 C18 analytic HPLC monitored in situ ligation between Ubi H-L$_1$-F$_{45}$-BMEA with peptide 6 with MESNa as the thiol additive. The ligation was analyzed at 0 h, 6.5 h and 10 h, respectively. Peak a: H-L$_1$-F$_{45}$-BMEA; peak b: 6; peak c: ligation product; peak d: H-L$_1$-F$_{45}$-BMEA and H-L$_1$-F$_{45}$-OH. HPLC gradient: 0% to 80% of buffer B in buffer A for 40 min.

Figure 19:
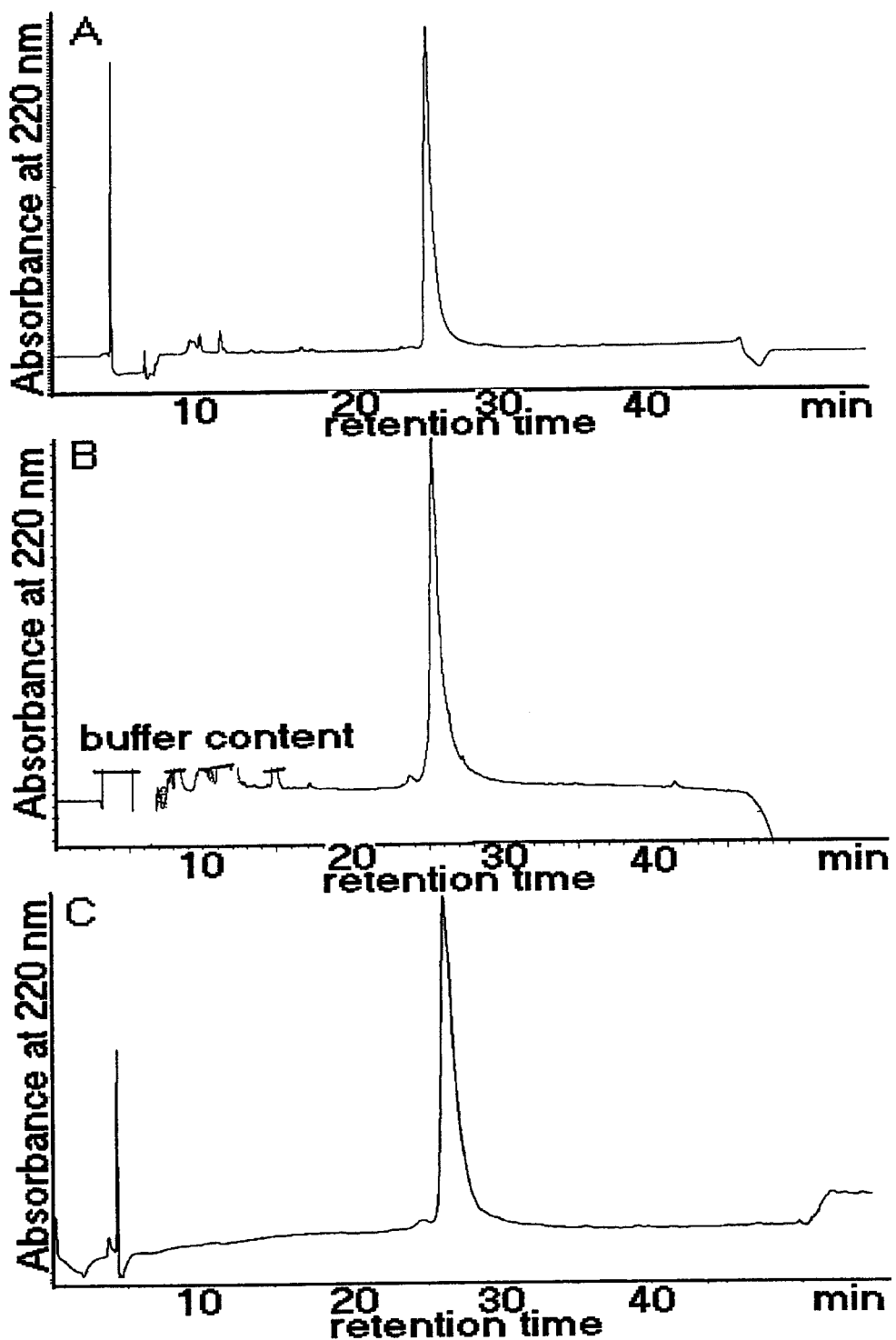

FIG. 19 The conversion of Cys28 and Cys 46 in synthesized ubiquitin to Ala by free radical mediated desulfurization. A). C18 analytic HPLC of purified ubiquitin Cys28Cys46. B). C18 analytic HPLC analysis of the desulfurization after 8 hours. C). C18 analytic HPLC of purified desulfurization product. D). The raw and deconvoluted ESI MS of the desulfurization product. MW found 8546.8, calculated 8546.70.

Figure 20:
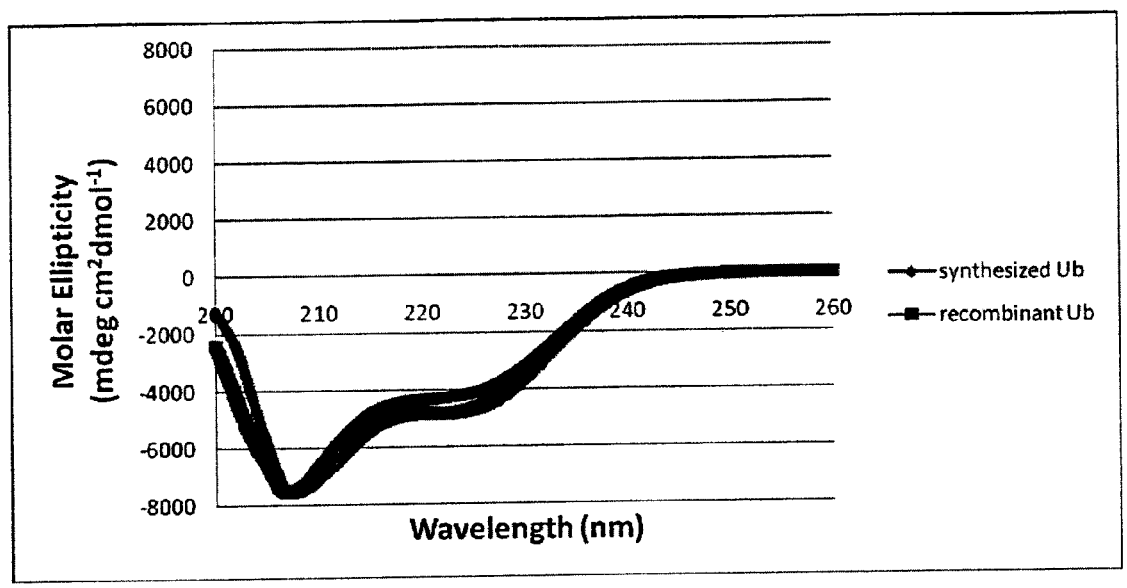

FIG. 20 The circular dichroism (CD) spectra of the refolded synthesized monoubiquitin and its recombinant counterpart.

Figure 21:
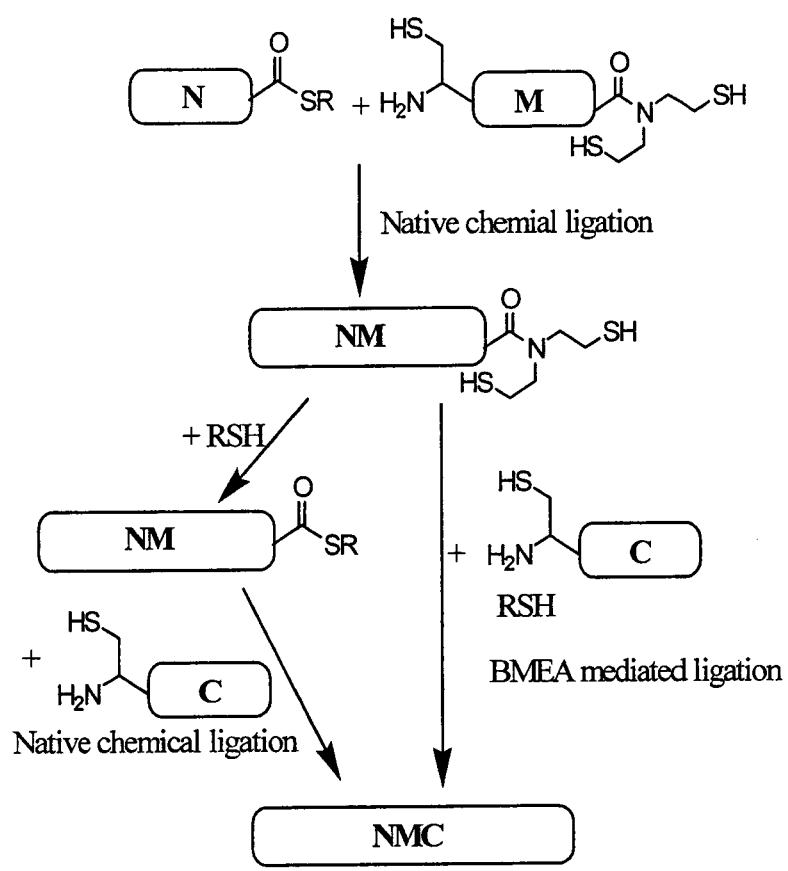

FIG. 21 The N to C sequential ligation using the combination of NCL and BMEA mediated ligation. Preferably R is an alkyl or aryl group. In the most common cases the SR part is from HSCH2CH2CONH2, HSCH2CH2COOH, benzylmercaptan, MESNa, methyl mercaptoacetate or another thiol compound.

Figure 22:
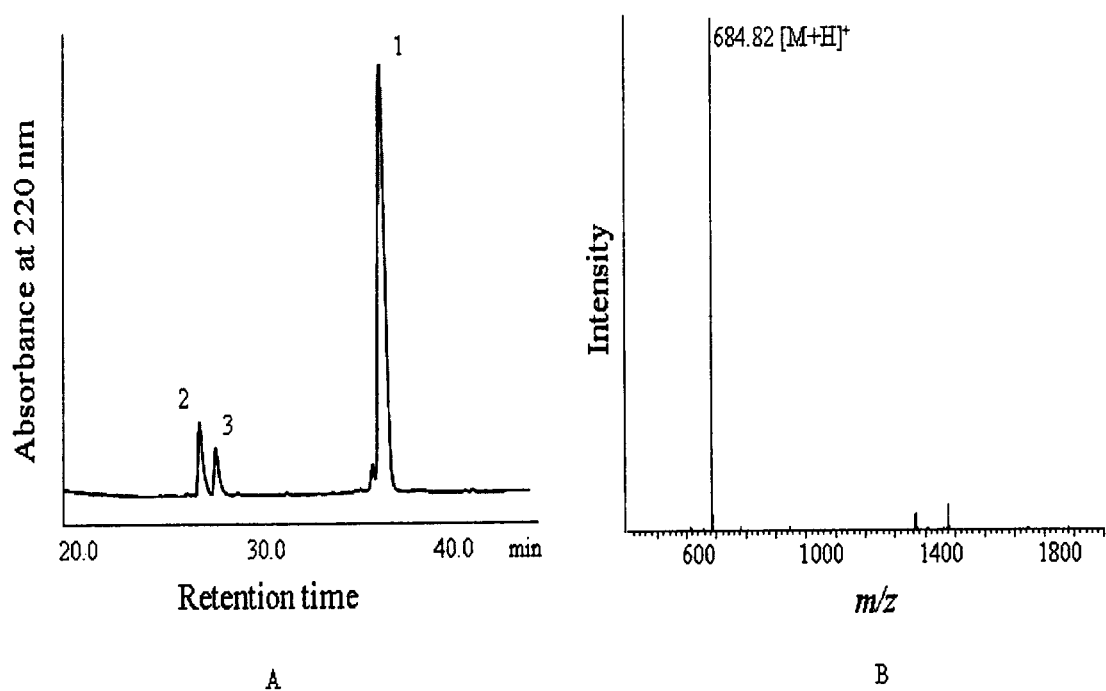

FIG. 22 Characterization of peptide H-LKSFG-(NCH$_2$CH$_2$SH, CH$_2$CH$_2$CH$_2$SH) (SEQ ID NO:9). (A) C18 analytical HPLC profile of H-LKSFG-(NCH$_2$CH$_2$SH, CH$_2$CH$_2$CH$_2$SH) (SEQ ID NO:9). HPLC conditions: 0% to 45% of buffer B in buffer A in 45 min. Peak 1 is peptide LKSFG-(NCH$_2$CH$_2$SH, CH$_2$CH$_2$CH$_2$SH) (SEQ ID NO:9), and peak 2 & 3 are the thioesters form of peptide LKSFG-(NCH$_2$CH$_2$SH, CH$_2$CH$_2$CH$_2$SH) (SEQ ID NO:9). (B) Mass spectrum of this peptide determined by ESI-MS. [M+H]$^+$ found: 684.82, MW calcd: 683.9.

Figure 23:
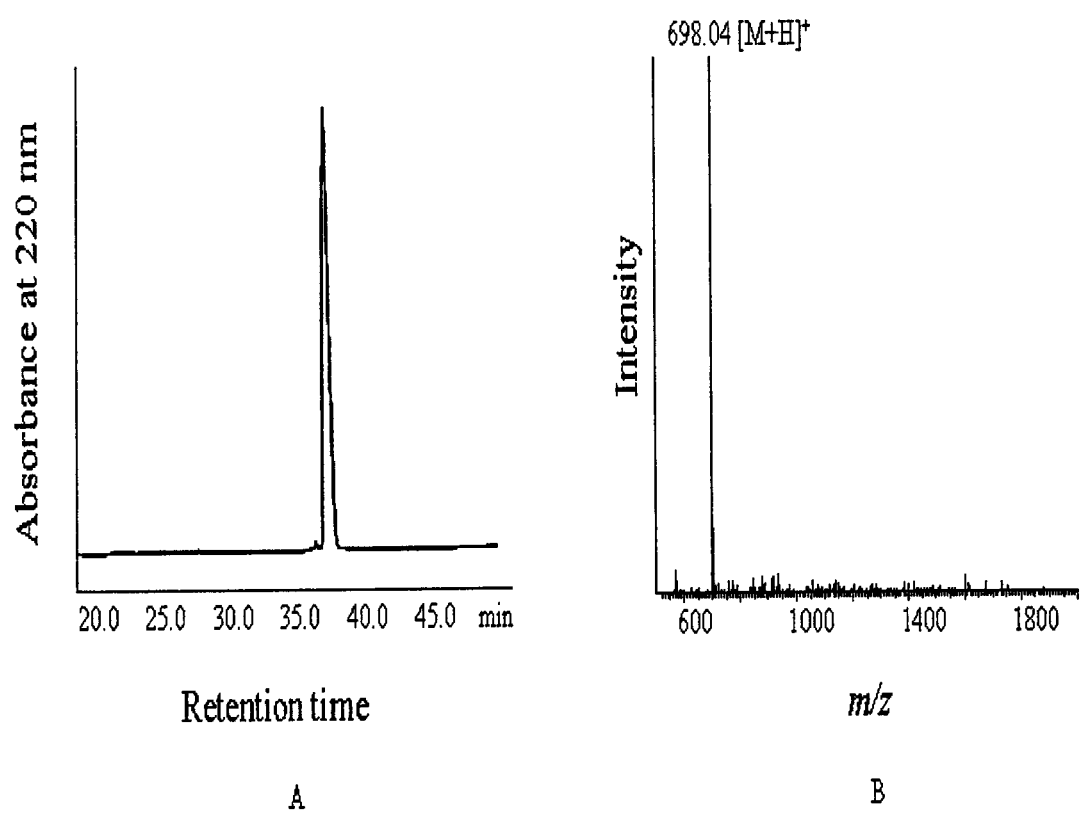

FIG. 23 Characterization of peptide LKSFG-N(CH$_2$CH$_2$CH$_2$SH)$_2$ (SEQ ID NO:10). (A) C18 analytical HPLC profile of LKSFG-(NCH$_2$CH$_2$CH$_2$SH)$_2$ (SEQ ID NO:11). HPLC conditions: 0% to 45% of buffer B in buffer A in 45 min. (B) Mass spectrum of this peptide determined by ESI-MS. [M+H]$^+$ found: 698.04, MW calcd: 697.1.

Figure 24:
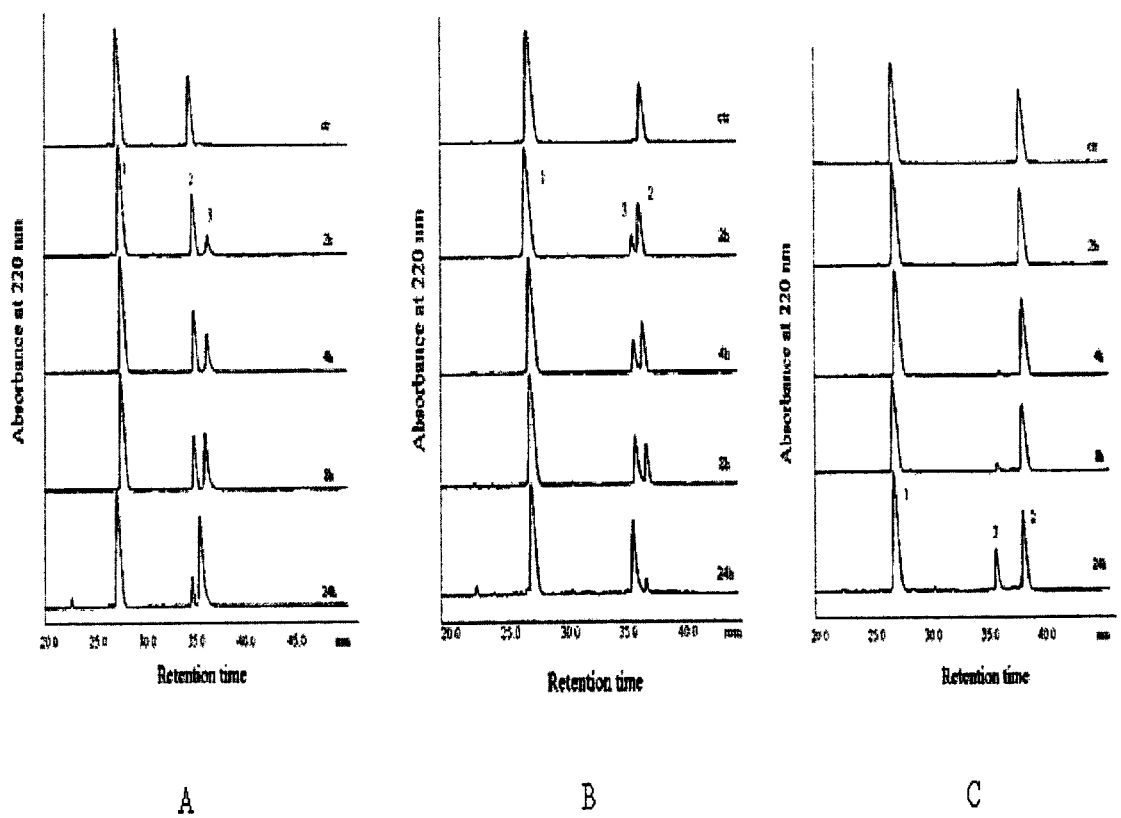

FIG. 24 Analytical HPLC analysis of the ligation reactions. The conditions were all the same except different dithiol peptides, A: H-LKSFG-BMEA (SEQ ID NO:3), B: H-LKSFG-N(CH$_2$CH$_2$SH, CH$_2$CH$_2$CH$_2$SH) (SEQ ID NO:12), C: H-LKSFG-N(CH$_2$CH$_2$CH$_2$SH)$_2$ (SEQ ID NO:10). HPLC conditions were all the same: 0% to 40% of buffer B in buffer A in 40 min. Peak 1 is peptide H-CLKFA-NH$_2$, peak 2 is dithiol peptide and peak 3 is the ligation product.

DEFINITIONS

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In the context of this specification, subject to the further definitions provided herein, the term "amino acid" is defined as having at least one primary, secondary, tertiary or quaternary amino group, and at least one acid group, wherein the acid group may be a carboxylic, sulfonic, or phosphonic acid, or mixtures thereof. The amino groups may be "alpha", "beta", "gamma" . . . to "omega" with respect to the acid group(s). The backbone of the "amino acid" may be substituted with one or more groups selected from halogen, hydroxy, guanido, heterocyclic groups. Thus term "amino acids" also includes within its scope glycine, alanine, valine, leucine, isoleucine, methionine, proline, phenylalanine, tryptophane, serine, threonine, cysteine, tyrosine, asparagine, glutamine, asparte, glutamine, lysine, arginine and histidine, taurine, betaine, N-methylalanine etc. (L) and (D) forms of amino acids are included in the scope of this invention.

As used herein, by 'Fmoc' is meant the protecting group 9H-fluoren-9-ylmethoxycarbonyl for use in solid-phase peptide synthesis, as well as the method of solid-phase peptide synthesis in which the N-termini of amino acid monomers are protected by the Fmoc protecting group before being added onto a deprotected amino acid chain.

As used herein, the substituent $R_2$ is a protecting group; any protecting group can be used provided it is suitable for use in the Fmoc process. In one embodiment, $R_2$ is a triphenylmethyl (Trt) group. In another embodiment, $R_2$ is selected from the group consisting of: 3-nitro-2-pyridine sulfenyl, tertiary-butyl (t-butyl), 2-pyridine-sulfenyl, methyl-sulfenyl or acetamidomethyl.

The Linker may be any linker suitable for use in the Fmoc process. In one embodiment, the linker may be the same substituent as the R2 group. In one embodiment, the linker can be a benzyl group or derivative, a phenyl group or derivative or a peptidyl group or derivative. In one embodiment, the linker is a triphenylmethyl (Trt) group.

The term 'resin' is to be interpreted broadly to include any resin suitable for use in solid-phase peptide synthesis. For example, the term resin includes any polymeric resin suitable for peptide synthesis, for example the resin is a polystyrene resin, for example, styrene cross-linked with 1-2% divinylbenzene; a polyacrylamide resin, polyethylene glycol (PEG)-polystyrene resin (PEG-PS), PEGA (polyethylene glycol dimethylacrylamide copolymer) resin or the resin is based on polystyrene, polyethylene glycol (PEG)-polystyrene or PEGA (polyethylene glycol dimethylacrylamide copolymer).

In one embodiment the resin is a glass bead, cellulose fibre or composite suitable for peptide synthesis.

The term 'amino acyl' is to be interpreted broadly to include any amino acid group forming the required R—CO group, or a derivative thereof having a required R—CO group.

The term "protein" as used in the context of the present specification can be used synonymously with the term "polypeptide", unless the context indicates otherwise. The term "protein" may include a complex of two or more polypeptides which can be linked by bonds other than peptide bonds (e.g. disulfide bonds).

The term 'peptidyl' is to be interpreted broadly to include any peptide in which the C-terminal amino acid forms the required R—CO group, or a derivative thereof having a required R—CO group. The peptide can be a short peptide chain of from 2 to 15 amino acids, or from 2 to 30 amino acids. The definition of peptide as used herein also includes oligopeptides and polypeptides: essentially, any length of peptide chain is included in this definition (e.g. including peptides greater than 5, 10, 15, 20, 25 or 30 amino acids), provided it is suitable for use in the present invention.

In one embodiment, formula (I) as used herein can also include the product of an intramolecular thiolysis reaction to produce a thioester.

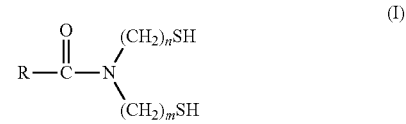

(I)

Formula (I) is suitable for use in native chemical ligation reaction without the requirement for any prior step for conversion to a thioester.

The thioester product of an intramolecular thiolysis reaction of Formula (I) is shown below

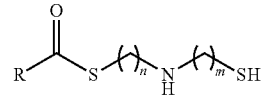

In one embodiment, the substituent 'R—CO' is an amino acyl or peptidyl group, or a derivative thereof having a required R—CO group. The substituent "R" may also refer to one or more groups independently selected from hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$.

The term "hydroxyl" as used herein refers to the functional group —OH.

The term "alkoxy" as used herein refers to straight chain or branched alkyloxy groups. Examples include methoxy, ethoxy, n-propoxy, isopropoxy, tert-butoxy, and the like.

The term "thiol" means —SH.

The term "thioether" refers to ether groups wherein the oxygen is replaced with a sulfur. The thioether groups include but are not limited to -alkylene-S-alkyl, -alkylene-S-aryl, -alkylene-S-arylalkyl, -alkylene-S-alkylaryl, -aryl-S-alkyl, -aryl-S-aryl, -aryl-S-alkylaryl, -aryl-S-arylalkyl, -arylalkyl-S-alkyl, -arylalkyl-S-aryl, -arylalkyl-S-alkylaryl, -arylalkyl-S-arylalkyl, -alkylaryl-S-alkyl, -alkylaryl-S-aryl, -alkylaryl- S-alkylaryl, and -alkylaryl-S-arylalkyl. The thioether groups may be optionally substituted with a substituent as described above.

The term "thiol additive" as used in the context of the present specification is to be interpreted broadly and includes compounds with a thiol (—SH—) group that catalyze the formation of thioesters.

The term "nucleophile" as used herein refers to a chemical moiety that has a reactive pair of electrons and that participates in a chemical reaction by donating electrons, i.e., nucleophiles are electron donor compounds. The nucleophile may be a halogen, nitrogen, sulfur or oxygen nucleophile. Exemplary nucleophiles include fluorides, cyanides, iodides, chlorides, bromides, acetates, enolates, primary amines, secondary amines, amino, alkoxides, thiols, alkyl sulfides (such as mercaptans), hydroxides, azides, and hydrazines, among others.

The term "amino" as used herein refers to groups of the form —$NR_a$ or —$NR_aR_b$ wherein $R_a$ and $R_b$ are independently selected from the group including but not limited to hydrogen, optionally substituted alkyl, optionally substituted alkenyl, optionally substituted alkynyl, optionally substituted alkoxy and optionally substituted aryl groups. For example, the term "amino" as used herein may be used to refer to an —NH group at the $R_2$ and/or $R_3$ position of a compound of formula (I), or to an —$NHCH_3$ group in the optionally substituted aliphatic group at the T position of a compound of formula (I).

The term "aliphatic" refers to a linear, branched, or cyclic alkyl, alkenyl, or alkynyl group.

The term "alkyl" includes within its meaning monovalent ("alkyl") and divalent ("alkylene") straight chain or branched chain saturated aliphatic groups having from 1 to 10 carbon atoms, e.g., 1, 2, 3, 4, 5, 6, 7, 8, 9, or 10 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "lower alkyl" refers to a straight or branched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-pentyl, n-hexyl, and the like.

The term "alkenyl" includes within its meaning monovalent ("alkenyl") and divalent ("alkenylene") straight or branched chain unsaturated aliphatic hydrocarbon groups having from 2 to 10 carbon atoms, e.g., 2, 3, 4, 5, 6, 7, 8, 9, or 10 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pentenyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptenyl, 3-heptenyl, 1-octenyl, 1-nonenyl, 1-decenyl, and the like.

The term "lower alkenyl" refers to a straight or branched saturated hydrocarbon chain having 2, 3, 4, 5, or 6 carbon atoms.

The term "alkynyl" as used herein includes within its meaning monovalent ("alkynyl") and divalent ("alkynylene") straight or branched chain unsaturated aliphatic hydrocarbon groups having from 2 to 10 carbon atoms and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, 1-methylpentynyl, 1-heptynyl, 2-heptynyl, 1-octynyl, 2-octynyl, 1-nonyl, 1-decynyl, and the like.

The term "lower alkynyl" refers to a straight or branched saturated hydrocarbon chain having 2, 3, 4, 5, or 6 carbon atoms.

The term "heteroatom" or variants such as "hetero-" as used herein refers to oxygen (O), nitrogen (N), phosphorus (P) and sulfur (S).

The term "aryl" or variants such as "aromatic group" or "arylene" as used herein refers to single, polynuclear, conjugated and fused residues of aromatic hydrocarbons having from 6 to 10 carbon atoms. Exemplary aryl groups include, but are not limited to phenyl, naphthyl, tetrahydronaphthyl, and the like.

The term "heteroaryl" and variants such as "heteroaromatic group" or "heteroarylene" as used herein, includes within its meaning single, polynuclear, conjugated and fused aromatic moieties having 5 to 20 atoms wherein 1 to 6 atoms are heteroatoms selected from O, N, NH and S. Examples of such groups include pyridyl, 2,2'-bipyridyl, phenanthrolinyl, quinolinyl, thiophenyl, indoyl, furanyl and pyrrolyl moieties and the like.

The term "cycloalkyl" as used herein refers to cyclic saturated aliphatic groups and includes within its meaning monovalent ("cycloalkyl"), and divalent ("cycloalkylene"), saturated, monocyclic, bicyclic, polycyclic or fused polycyclic hydrocarbon radicals having from 3 to 10 carbon atoms, eg, 3, 4, 5, 6, 7, 8, 9, or 10 carbon atoms. Examples of cycloalkyl groups include but are not limited to cyclopropyl, 2-methylcyclopropyl, cyclobutyl, cyclopentyl, 2-methylcyclopentyl, 3-methylcyclopentyl, cyclohexyl, and the like.

The term "cycloalkenyl" as used herein, refers to cyclic unsaturated aliphatic groups and includes within its meaning monovalent ("cycloalkenyl") and divalent ("cycloalkenylene"), monocyclic, bicyclic, polycyclic or fused polycyclic hydrocarbon radicals having from 3 to 10 carbon atoms and having at least one double bond, of either E, Z, cis or trans stereochemistry where applicable, anywhere in the alkyl chain. Examples of cycloalkenyl groups include but are not limited to cyclopropenyl, cyclopentenyl, cyclohexenyl, and the like.

The term "heterocycloalkyl" as used herein, includes within its meaning monovalent ("heterocycloalkyl") and divalent ("heterocycloalkylene"), saturated, monocyclic, bicyclic, polycyclic or fused hydrocarbon radicals having from 3 to 10 ring atoms wherein 1 to 5 ring atoms are heteroatoms selected from O, N, NH, or S. Examples include pyrrolidinyl, piperidinyl, quinuclidinyl, azetidinyl, morpholinyl, tetrahydrothiophenyl, tetrahydrofuranyl, tetrahydropyranyl, and the like.

The term "heterocycloalkenyl" as used herein, includes within its meaning monovalent ("heterocycloalkenyl") and divalent ("heterocycloalkenylene"), saturated, monocyclic, bicyclic, polycyclic or fused polycyclic hydrocarbon radicals having from 3 to 10 ring atoms and having at least 1 double bond, wherein from 1 to 5 ring atoms are heteroatoms selected from O, N, NH or S.

The term "halide" or variants such as "halogen" or "halo" as used herein refers to fluoride, chloride, bromide and iodide.

DETAILED DESCRIPTION OF THE INVENTION

In a first aspect of the present invention there is provided a carboxyamide compound having the following structural formula, in which, independently, n=2 or 3 and m=2 or 3

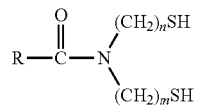

and in which RCO is an amino acyl or peptidyl group, or in which R is one or more groups independently selected from hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$.

In one embodiment both n and m=2. In a further embodiment n=2, and m=3. In a further embodiment n=3 and m=2. In a further embodiment both n and m=3.

In one embodiment, R—CO— is an amino acyl or peptidyl group.

As discussed herein, the compounds of the invention can advantageously be prepared using Fmoc solid phase peptide synthesis. Accordingly, the present invention provides for the step of synthesising a compound of the invention by Fmoc solid phase peptide synthesis.

In a second aspect of the present invention there is provided a dialkylamine resin having the following formula:

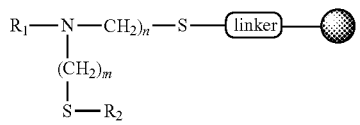

in which:

(ie. the circular shape in the formula) represents a resin or solid support n=independently 2,3; m=independently 2,3

$R_1$ is H, Fmoc $R_2$ is H or a protecting group such as Trt (trityl or triphenylmethyl);

and "linker" is any linker compatible with Fmoc chemistry, including a benzyl derivative or Trt.

In one embodiment both n and m=2. In a further embodiment n=2, and m=3. In a further embodiment n=3 and m=2. In a further embodiment both n and m=3.

In a third aspect of the present invention there is provided a dialkylamine resin having the following formula:

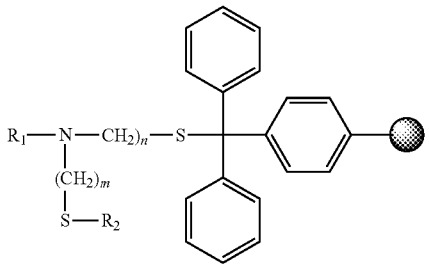

n=2, 3; m=2, 3
$R_1$=H, Fmoc
$R_2$=Trt
and in which

(ie. the circular shape in the formula) represents a resin or solid support.

In one embodiment both n and m=2. In a further embodiment n=2, and m=3. In a further embodiment n=3 and m=2. In a further embodiment both n and m=3.

In a fourth aspect of the present invention there is provided a compound having the following structural formula, in which, independently, n=2 or 3 and m=2 or 3

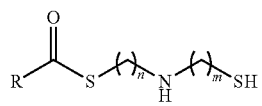

and in which RCO is an amino acyl or peptidyl group, or in which R is one or more groups independently selected from hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$.

In one embodiment of the present invention, the dialkylamine resin described herein further comprises at least one amino acid, amino acyl group or peptidyl group as described herein.

It is envisaged that the compounds and resins of the invention will find utility in methods of peptide, polypeptide and protein synthesis. Accordingly, a fifth aspect of the present invention provides a method of peptide synthesis comprising a compound as described herein, or a resin as described herein. Similarly, in a sixth aspect of the present invention there is provided a method of protein synthesis comprising a compound as described herein, or a resin as described herein.

In one embodiment, the method of the fifth or sixth aspect comprises the use of a compound or resin as described herein in NCL. The compounds and resins of the invention can be used directly in NCL and thus in at least some embodiments the compounds and resins are so used.

In one embodiment the method of the fifth or sixth aspect of the invention comprises the synthesis of a peptide of at least 3, 4, 5, 10, 20, 30, 40, 50, 60, 70 or 80 amino acids long.

The methods of the fifth and sixth aspect of the invention may further comprise the step of purifying and obtaining the peptide or protein respectively.

In a seventh aspect of the present invention there is provided a process for the production of a dialkylamine resin as described herein, comprising the following steps:

(i) reaction of formula (A) below with o-NO$_2$PhSO$_2$—Cl, DIEA, and CH$_2$Cl$_2$-DMF to obtain formula (B)

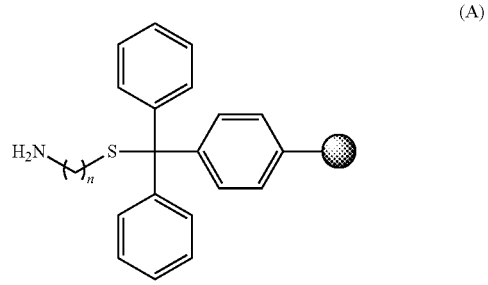

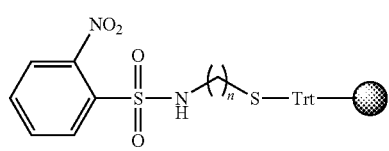

(ii) alkylation of formula (B) and thiolytic removal of the sulfonyl group to obtain formula (C)

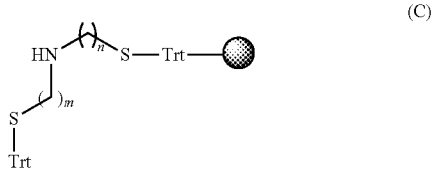

The dialkylamine resin can also be produced by directly loading the dialkylamine, HS(CH$_2$)$_m$NH(CH$_2$)$_n$SH, to a trityl resin.

In one embodiment of the present invention, the process for the production of a dialkylamine resin further comprises the step of Fmoc SSPS followed by cleavage to obtain formula (D):

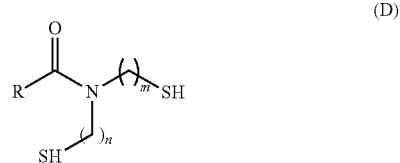

in which n=2 or 3 and m=2 or 3; and in which RCO is an amino acyl or peptidyl group, or in which R is one or more groups independently selected from hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$ In one embodiment both n and m=2. In a further embodiment n=2, and m=3. In a further embodiment n=3 and m=2. In a further embodiment both n and m=3.

In an eighth aspect of the present invention there is provided a process for the production of a peptide comprising a C-terminal tertiary N,N-bis(2-mercaptoethyl)-amide group; N-(2-mercaptoethyl)-N-(3-aminopropyl)-amide group or N,N-bis(3-mercaptopropyl)-amide, the process comprising the step of providing a dialkylamine resin as described herein. In a further embodiment, the process further comprises the step of purifying and obtaining the peptide comprising a C-terminal tertiary N,N-bis(2-mercaptoethyl)-amide group; N-(2-mercaptoethyl)-N-(3-aminopropyl)-amide group or N,N-bis(3-mercaptopropyl)-amide group.

In one embodiment of the present invention described herein, the process for production of a peptide comprises Fmoc solid-phase peptide synthesis. Thus, the fifth, sixth and eighth aspects of the invention may comprise Fmoc solid-phase peptide synthesis.

In an embodiment of the present invention in which the process is for production of a peptide described herein, and in which the process comprises Fmoc solid-phase peptide synthesis, and in which the process comprises the step of providing a dialkylamine resin as described herein, R$_2$ is Trt.

In a further embodiment, the process for production of a peptide or protein as described herein (e.g. according to the fifth, sixth and eighth aspects of the invention) comprises native chemical ligation. As discussed herein, NCL can conveniently be performed without the requirement for any prior step to thioester conversion.

In one embodiment the pH of the native chemical ligation is between 3 and 7, for example the pH is between 4 and 6. In a further embodiment, the reaction temperature of the native chemical ligation is between 20° C. and 50° C., for example between 25° C. and 50° C. or between 30° C. and 45° C.

The compounds and resins of the invention can be used directly in NCL and thus in at least some embodiments the compounds and resins are so used.

In one embodiment of the fifth, sixth and eighth aspects of the invention the method comprises at least two ligation steps. Methods of ligation include NCL and, where BMEA moieties are used, BMEA-mediated ligation (the skilled person will appreciate that equivalent ligation methods may be used when at least one of, or both of, n and m=3). Preferably, the pH for the ligation is between 3 and 7, for example the pH is between 4 and 6.

In one embodiment at least one of the ligation steps (e.g. at least the first ligation step) is NCL.

For the second step of ligation options include: (i) converting the ligation product to a thioester and performing NCL between the thioester and a C-terminal cys-peptide; and (ii) allowing the ligation product to directly react with the cys-peptide in situ. Optionally, one or more further ligation steps may follow.

In one embodiment the fifth, sixth and eighth aspects of the invention comprise N to C sequential ligation through the combination of native chemical ligation and peptidyl N,N-bis (2-mercaptoethyl)-amide mediated ligation.

In one embodiment of the fifth, sixth and eighth aspects of the invention the method comprises N to C sequential ligation according to the scheme as shown in FIG. 21.

A further aspect of the invention comprises a peptide (including polypeptides and proteins) obtainable by a method of the fifth, sixth, eighth or ninth aspects of the invention. A peptide or protein produced in accordance with the invention may optionally undergo one or more processing steps and/or purification. For example, one or more (and optionally all) cysteine residues at one or more (and optionally all) of the ligation junctions may be converted to other amino acid residues. Free radical mediated desulfurization may be used for such a process. Other processing steps may include folding of the peptide or protein e.g. to its native state. This may for example be achieved by dialysis. The processing and/or purification steps may occur in any order. In some embodiments, purification follows one or more processing steps. In some embodiments one or more processing steps follows purification.

In one embodiment of the process for production of a peptide or a method of peptide synthesis described herein, the process further comprises the addition of a thiol additive, in which the thiol additive is an alkyl thiol, benzylmercaptan, MESNa, methyl mercaptoacetate or another thiol compound.

In a further embodiment of the process for production of a peptide or a method of peptide synthesis described herein, the method or process comprises use of microwave radiation.

In a further embodiment of the process for production of a peptide or a method of peptide synthesis described herein, the C-terminal amino acid is ALA, ARG, ASN, ASP, CYS, GLU, GLN, GLY, HIS, LEU, LYS, MET, PHE, PRO, SER, TRY or TYR or the RCO group is an amino acyl group of ALA, ARG, ASN, ASP, CYS, GLU, GLN, GLY, HIS, LEU, LYS, MET, PHE, PRO, SER, TRY or TYR. For example, the C-terminal amino acid or RCO group is the amino acid GLY, ALA, SER, PHE, LEU, MET, ASN, TYR, TRP or LYS or an amino acyl group thereof.

In a ninth aspect of the present invention there is provided a method of thioester peptide synthesis comprising an exchange reaction of a compound as described herein with a thiol-containing compound (R'SH) in an acidic solution (H+), for example as shown in the reaction schematic below:

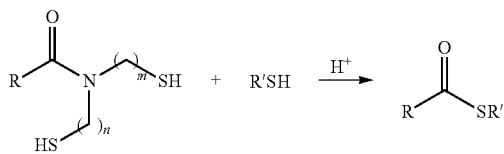

in which, independently, n=2 or 3 and m=2 or 3, and in which RCO is an amino acyl or peptidyl group, or in which R is one or more groups independently selected from hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$ In one embodiment both n and m=2. In a further embodiment n=2, and m=3. In a further embodiment n=3 and m=2. In a further embodiment both n and m=3.

In one embodiment, the thiol-containing compound is 3-mercaptopropionic acid or benzylmercaptan or methyl mercaptoacetate or MESNa.

The thioester peptides of the invention can be used for NCL or for other applications.

As mentioned above, whilst various references are made herein to BMEA/BMEA moieties, the invention is not limited to such moieties and, as such, references herein to BMEA/BMEA moieties apply mutatis mutandis to variants of BMEA/BMEA moieties as taught herein, unless the context indicates otherwise. In this regard, we have designed a new BMEA variant in which cysteine is used to replace a mercaptoethylamine. Its carboxyl group can be used to attach the variant to a Rink amide resin or other resin type:

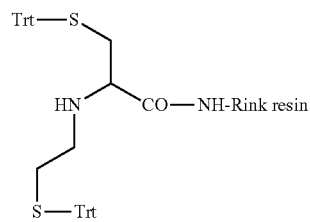

Accordingly, in the above-described aspects of the invention a BMEA variant in which a cysteine replaces a mercaptoethylamine may be used in place of a BMEA moiety.

A tenth aspect of the invention comprises the use of methyl mercaptoacetate as a thiol additive for native chemical ligation.

The present invention includes within its scope all isomeric forms of the compounds disclosed herein, including all diastereomeric isomers, racemates and enantiomers. Thus, compounds of formula (I) and derivatives thereof should be understood to include, for example, E, Z, cis, trans, (R), (S), (L), (D), (+), and/or (−) forms of the compounds, as appropriate in each case.

Unless specified otherwise, the terms "comprising" and "comprise", and grammatical variants thereof, are intended to represent "open" or "inclusive" language such that they include recited elements but also permit inclusion of additional, unrecited elements.

Non-limiting examples of the invention will be further described in greater detail by reference to specific Examples, which should not be construed as in any way limiting the scope of the invention.

EXAMPLES

Example 1

Results and Discussion

Synthesis of peptide N,N-bis(2-mercaptoethyl)-amides.

For the synthesis of a C-terminal BMEA peptide 1 shown in Scheme 2, we designed a bis(2-mercaptoethyl)amine-derived trityl resin 5 which was prepared in straightforward reaction steps (Scheme 3). Thus, (2-aminoethyl)sulfanyl-trityl resin 3 was reacted with o-nitrobenzenesulfonyl chloride to afford the sulfonamide resin 4. Alkylation of the sulfonamide with Trt-SCH$_2$CH$_2$OH by Mitsunobu reaction and subsequent thiolytic removal of the sulfonyl group yielded finally the dialkylamine resin 5, ready for use in Fmoc SPPS.

Scheme 3. Synthesis of C-terminal N,N-bis(2-mercaptoethyl)-amide (BMEA) peptides.

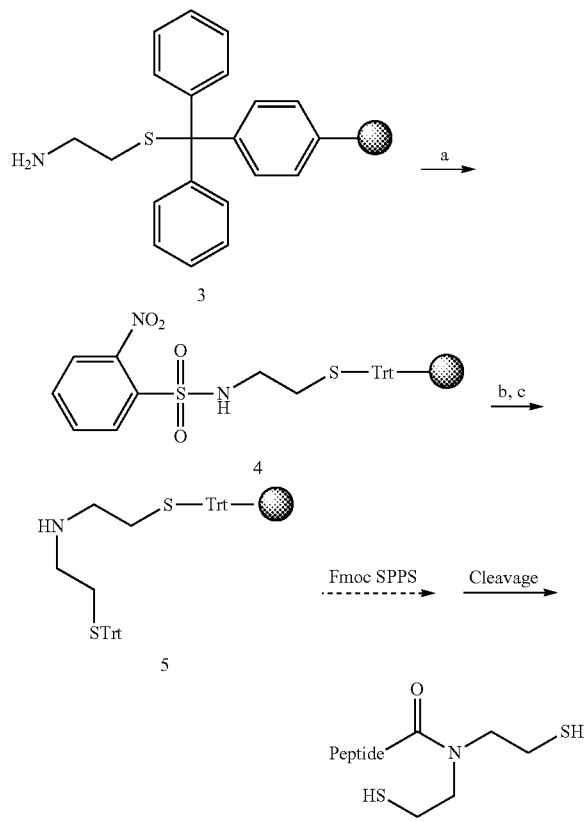

(a) o-NO$_2$PhSO$_2$—Cl, DIEA, CH$_2$Cl$_2$—DMF;
(b) Trt-SCH$_2$CH$_2$OH, Ph$_3$P, DEAD, THF—CH$_2$Cl$_2$;
(c) HSCH$_2$CH$_2$OH, DBU, DMF.

Loading the 1$^{st}$ Fmoc-amino acid onto resin 5 was achieved using DIC/HOAt, a coupling protocol known to be effective for a sterically hindered 2° amine with minimum risks of racemization. Subsequent assembling of the peptide chain was effected using standard SPPS procedures. Because of its inactivated nature, the tertiary amide linkage is completely stable during Fmoc SPPS.

Model Study with a C-Ter Gly BMEA Peptide.

Figure 1:
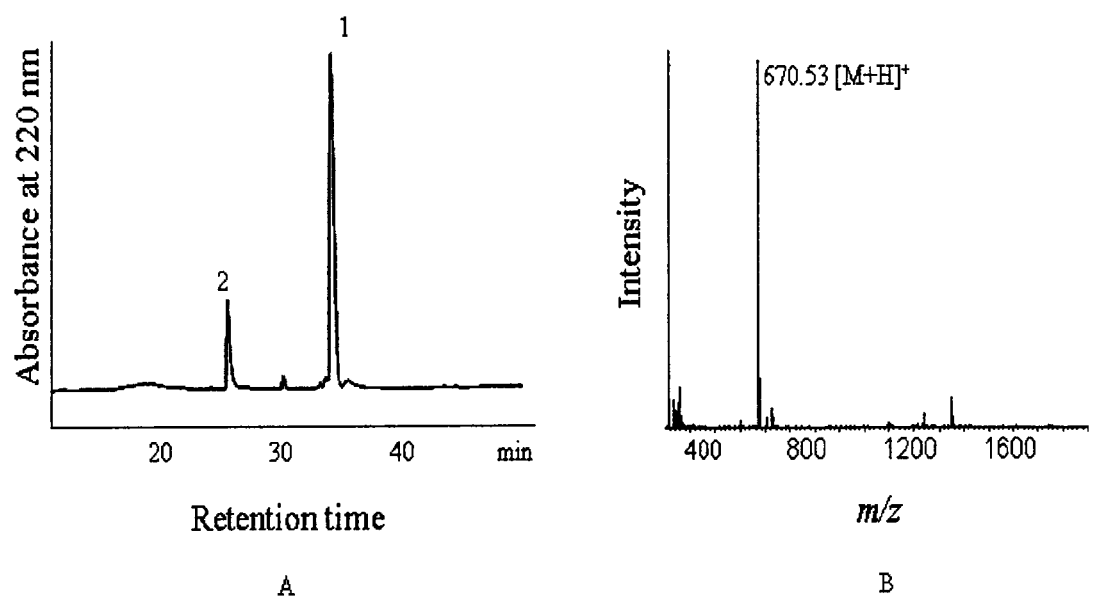
FIG. 1. HPLC and MS analyses of LKSFG-(NCH$_2$CH$_2$SH)$_2$. Panel A: HPLC profile; panel B: ESI-MS.
Figure 2:
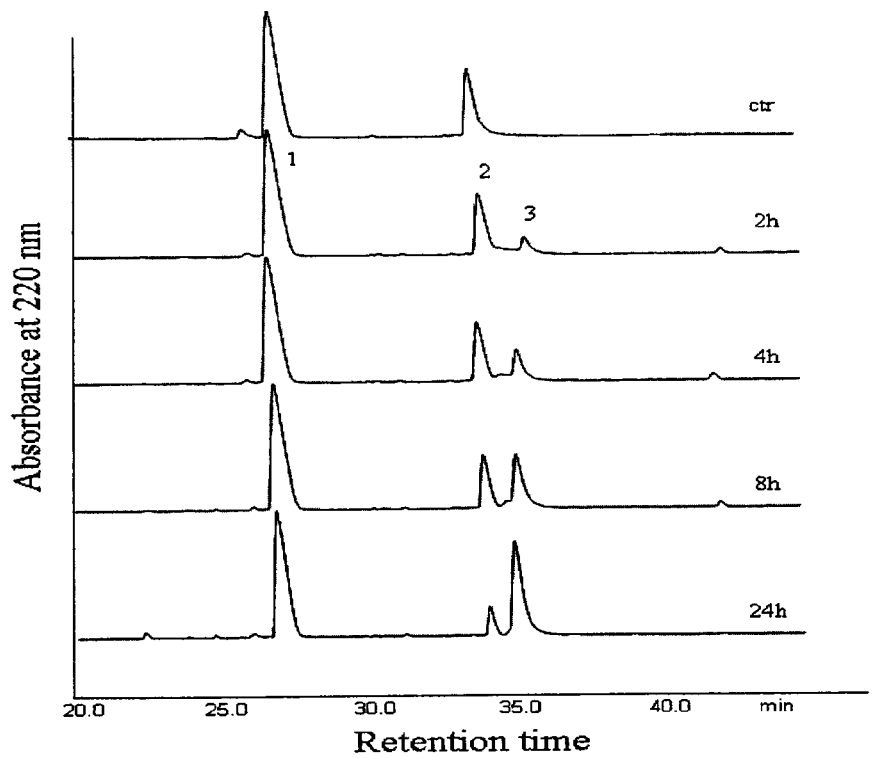
FIG. 2. Ligation of LKSFG(CH$_2$CH$_2$SH)$_2$ (SEQ ID NO:1) with CLKFA (SEQ ID NO:2) at pH 4 (top panel) and pH 5 (bottom panel). The reaction situation was checked by analytical RP-HPLC at 2 hrs, 4 hrs, 8 hrs and 24 hrs (FIG. 14). HPLC conditions were all the same: 0% to 40% of buffer B in buffer A in 40 min. Buffer A: 0.045% TFA in H$_2$O, buffer B: 90% acetonitrile in H$_2$O. Peak 1 is CLKFA, peak 2 is LKSFG (CH$_2$CH$_2$SH)$_2$ dithiol peptide, and peak 3 is the ligation product. No side reactions were detected.
Figure 2:
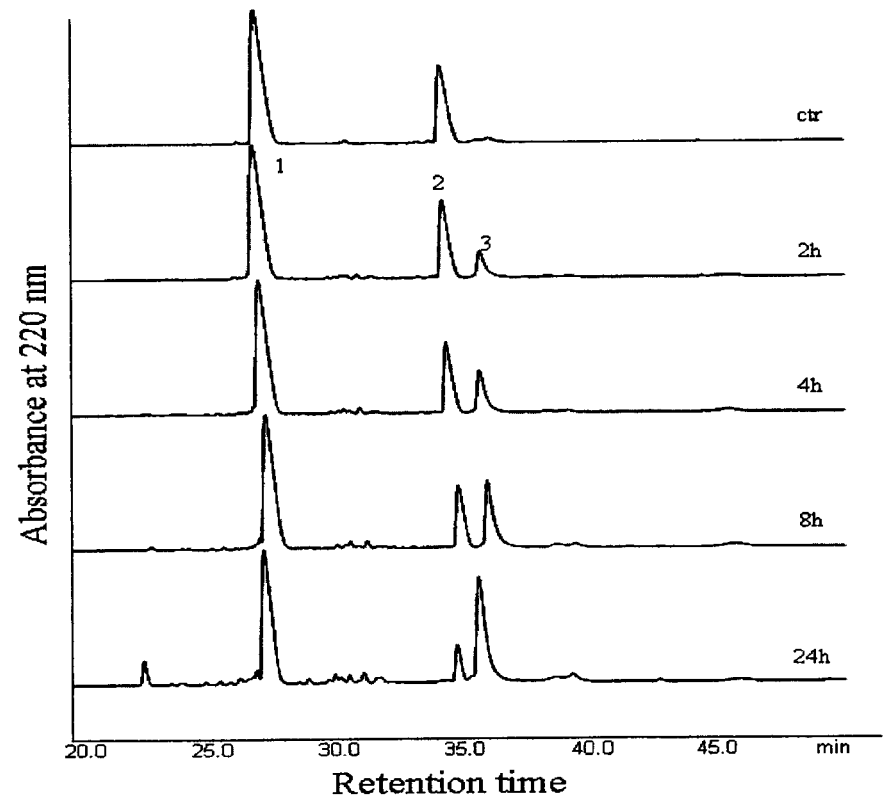

To test our BMEA-mediated ligation method, we first prepared a small BMEA peptide with a Gly as the C-terminal residue-LKSFG (SEQ ID NO:23). The crude product was of excellent quality as shown by HPLC analysis (FIG. 1). Interestingly, two peaks at a ratio of about 1:5 were seen from the HPLC profile. The smaller peak appeared to be the thioester form which, with a free amine in the BMEA portion, was expected to be more hydrophilic and would elute out earlier in HPLC, and the larger peak was the amide form. When the first or second peak was separated and reanalyzed by HPLC, the same two-peak pattern appeared, suggesting that the thioester form and amide form could quickly interchange in the HPLC buffer (pH~2). This result was very encouraging as it clearly showed that N—S acyl transfer could easily take place with this BMEA peptide under these relatively acidic conditions. In fact, when this peptide was treated with 20% mercaptopropionic acid (MPA) in H$_2$O, the MPA thioester was obtained in >85% yield after 8 h at room temperature. In previous studies with the N-alkyl cysteine method, thiol exchange with MPA yielded ~20% of the thioester product after 2 days of reaction at RT. These results show that the presence of two HS-Et groups on the amide nitrogen significantly increased the thioesterifying capability of BMEA as compared with N-alkyl cysteine systems.

We next wanted to test whether we can save the separate thiol-exchange reaction and its thioester product purification step and use the BMEA peptide directly for NCL, which would be ideal and is also the focus of our present study. To find the optimal pH range for the reaction, we first performed ligation of LKSFG-(NCH$_2$CH$_2$SH)$_2$ (SEQ ID NO:11) (5 mM) with CLKFA (SEQ ID NO:2) (15 mM) at different pH using benztlmercaptan (1%) as the thiol additive. The temperature of the reaction was 37° C. We found that when the reactions were conducted at pH 4, 5 and 6, the rate of ligation was about the same with about 75% of the BMEA peptide consumed to form the ligation product after 24 h. However, a slight increase of side products was seen at pH 6 (data not shown). When the pH was increased further to 7 and 8, significant side reactions were detected with a concomitant decrease of the reaction yield. The N-to-S acyl transfer appears to be the rate limiting step rate, as no significant amounts of the BMEA thioester or benzyl thioester were seen in HPLC, suggesting that, as soon as they were formed, these thioesters quickly reacted with the cysteinyl peptide CLKFA (SEQ ID NO:2).

We then chose pH 5 to conduct the ligation reaction at different temperatures. We found that the reaction was slower at room temperature with a consumption rate of about 50% of the BMEA peptide at 24 h. On the other hand, when the reaction was performed at 42° C., we observed 50% consumption at 8 h. After 24 h reaction, all the BMEA peptide was reacted.

Figure 3:
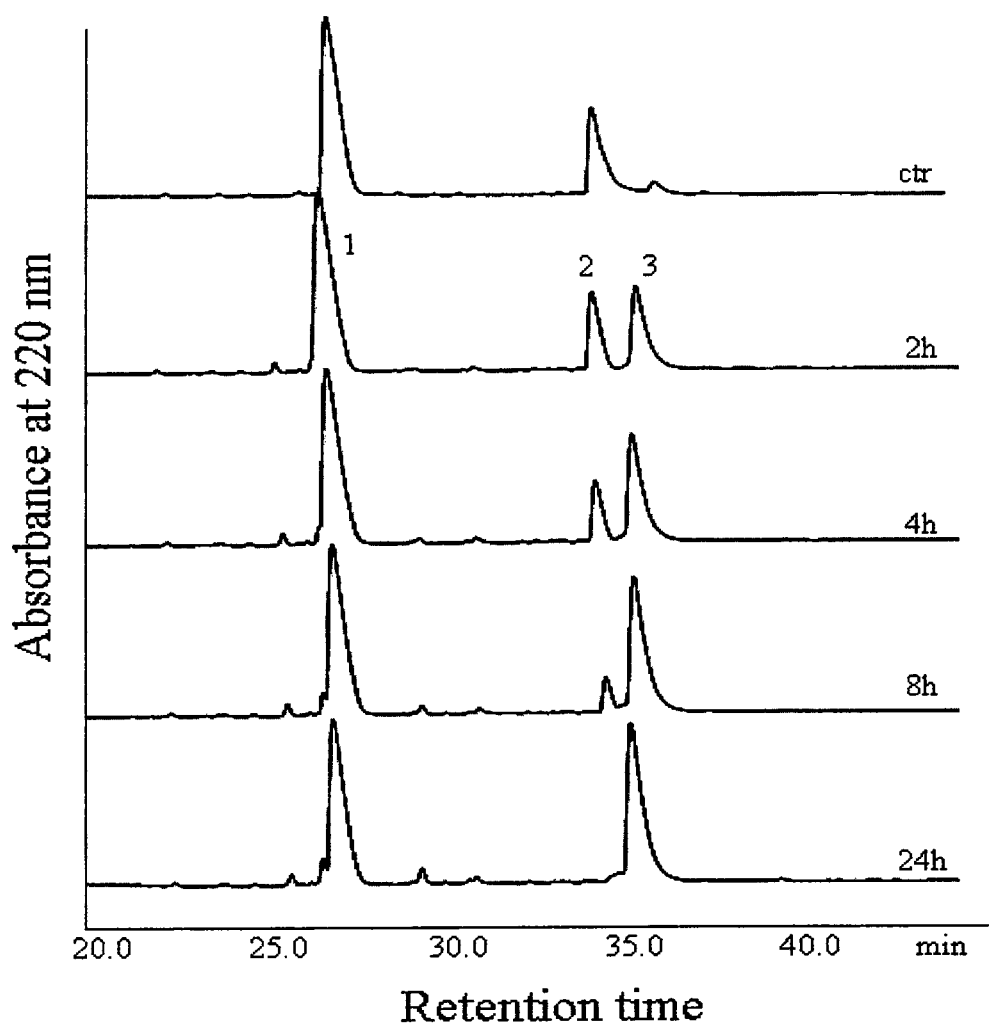
FIG. 3. Ligation between LKSFG(CH$_2$CH$_2$SH)$_2$ (SEQ ID NO:1) and CLKFA (SEQ ID NO:2) in the presence of MESNA, pH 5. The reaction situation was checked by analytical RP-HPLC at 2 hr, 4 hrs, 8 hrs and 24 hrs. HPLC conditions: 0% to 40% of buffer B in buffer A in 40 min. Buffer A: 0.045% TFA in H$_2$O, buffer B: 90% acetonatrile in H$_2$O. Peak 1 is CLKFA (SEQ ID No 2), peak 2 is the BMEA peptide LKSFG(CH$_2$CH$_2$SH)$_2$ (SEQ ID NO:1), and peak 3 is the ligation product.

We also found MESNA (HSCH$_2$CH$_2$SO$_3$Na) to be a better thiol additive for the ligation reaction. As we can see from FIG. 3, when the reaction was conducted at 37° C. and pH 5, the yield was ≥80% after 8 h in the presence 2% (w/v) MESNA.

Figure 4:
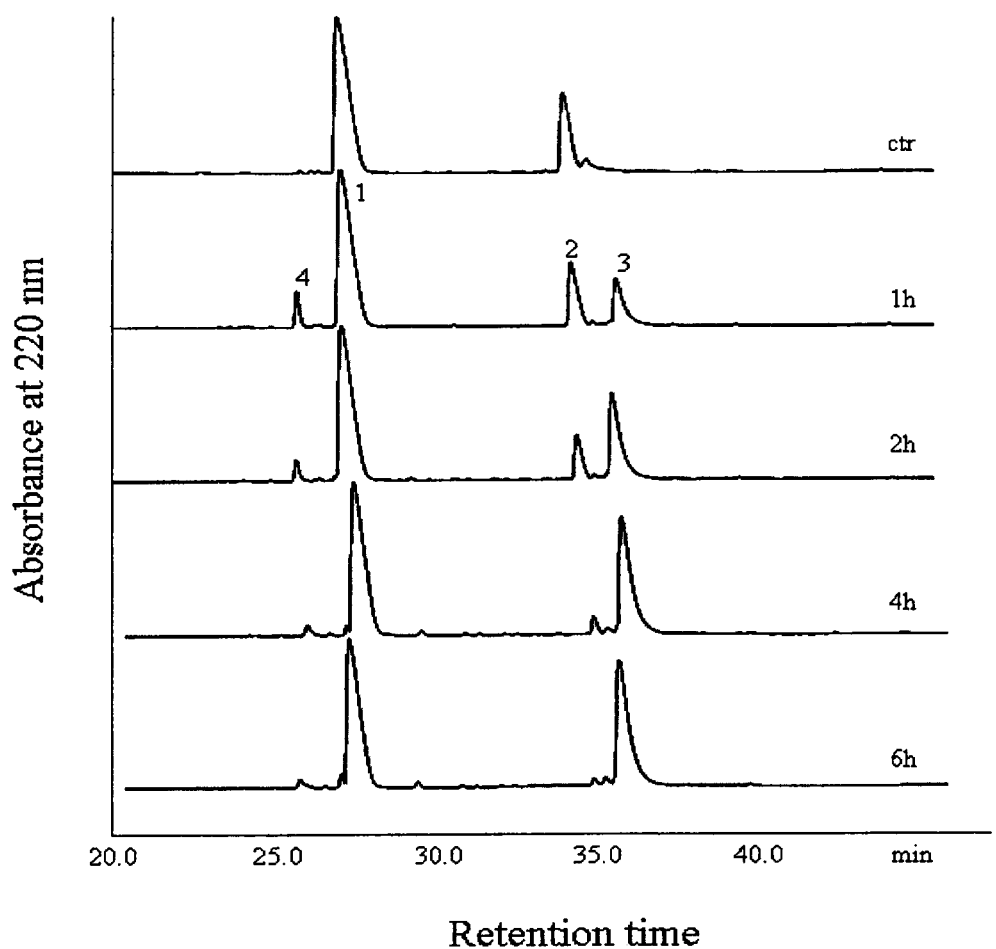
FIG. 4. Ligation conditions: pH 5, 2% MESNA, low power microwave irradiation. The reaction situation was checked by analytical RP-HPLC at 1 hr, 2 hrs, 4 hrs and 6 hrs. HPLC conditions were all the same: 0% to 40% of buffer B in buffer A in 40 min Buffer A: 0.045% TFA in H$_2$O, buffer B: 90% acetonatrile in H$_2$O. Peak 1 is CLKFA (SEQ ID NO:2), peak 2 is LKSFG(CH$_2$CH$_2$SH)$_2$ dithiol peptide (SEQ ID NO:1), peak 3 is the ligation product, and peak 4 is the LKSFG-MESN (SEQ ID NO:3).

We also found that microwave irradiation could significantly accelerate the reaction, as seen from FIG. 4. Basically, >90% yield was obtained after just 4 h reaction.

Other Model Studies—Reaction Scope of BMEA Peptides.

The above data clearly show that a peptide with a C-terminal BMEA can readily be converted to a thioester which can be ligated in situ with a cysteinyl peptide. To investigate the scope of this BMEA system, we then synthesized four other small BMEA peptides with different C-terminal amino acid residues, Ala, Ser, Phe and Val respectively (Table 1). These peptides were then used to in the ligation with CLKFA (SEQ ID NO:2) under microwave irradiation. The Findings were summarized in Table 1.

TABLE 1

Influence of the C-termial residue on the ligation yield of BMEA peptide LKSFX with CLKFA under microwave irradiation.

| time | C-terminal residue X | | | | |
|---|---|---|---|---|---|
| | G | A | S | F | V |
| 2 h | 65.20% | 61.90% | 58.70% | 50.80% | — |
| 4 h | 90.40% | 85.20% | 77.60% | 78.10% | — |
| 6 h | 98.50% | 94.00% | 89.60% | 91.90% | ≤5.00% |
| 8 h | 100% | 98% | 93.50% | 96.60% | — |
| 10 h | | 100% | 99% | 98.30% | — |

Ligation condition: pH 5, 2% MESNA, low power microwave irradiation.

From Table 1, one can draw the following conclusions. Although the reaction efficiency of BMEA peptide with a C-terminal Ala, Ser, or Phe was lower than that Gly due to steric hindrance, all the reactions were almost completed after 10 h. A C-ter Val seems to very detrimental to the reaction, as no more than 5% of product was formed after 6 h. As it was previously demonstrated in the literature that a C-ter Val thioester was able to perform native chemical ligation, the low reactivity of the BMEA peptide LKSFV must be due to its difficulty to undergo the N-to-S acyl transfer reaction. Nevertheless, these results show that, except for the sterically very hindered β-branched amino acids such as Val, ligation of BMEA peptides can tolerate most amino acids at the C-terminal position. This demonstrates the broad application scope of the tertiary amide BMEA system for native chemical ligation.

Synthesis of a Histone H3 Protein.

Having confirmed that BMEA peptides can be directly used for NCL in the above model studies, we then preceded with applying this method for protein synthesis. The semi-synthesis of a histone H3 protein through ligation between an N-terminal peptide of H3 and its C-terminal globular domain was demonstrated. Two peptides, H3(1-13) and H3(1-13)/K4me, corresponding to the N-terminal 13-residue sequence of H3 were synthesized as the C-terminal BMEA amide, and the H3 globular domain with an N-ter Cys, H3(14-135)K14C, was prepared recombinantly through over-expression in *E. coli*. The ligation reaction was conducted in a buffer (pH 6) containing 6 M Gdn-HCl, 50 mM TCEP, 2% (w/v) MESNA, and 2% (w/v) thiophenol sodium salt. Lyophilized H3(14-135)/K14C was dissolved in this ligation buffer at the final concentration of 2 mM and reacted with 3 eq. of H3(1-13)-BMEA and H3(1-13)/K4me-BMEA, respectively. The reaction incubated at 37° C. for 24-48 hours. The ligation reaction was monitored by C8 analytical RP-HPLC. The HPLC analysis and the mass spectral data of the ligation reactions were shown in FIG. 5.

HPLC conditions: 0% to 50% of buffer B in buffer A in 25 min. Buffer A, followed by 50% to 60% buffer B in Buffer A in 20 min. Buffer A: 0.3% TFA in $H_2O$, buffer B: 0.3% TFA and 90% acetonitrile in $H_2O$. 1 is the ligation product, and 2 is unligated H3(14-135)/K14C.

Figure 5A:
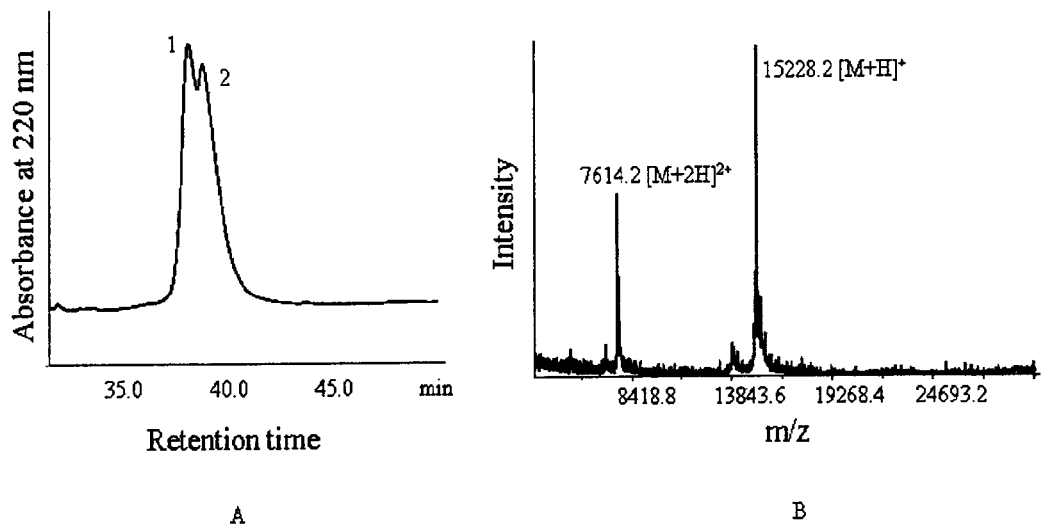
FIG. 5A. HPLC and MOLDI-MS analysis of ligation between H3(1-13)-BMEA and H3(14-135)/K14C.
Figure 5B:
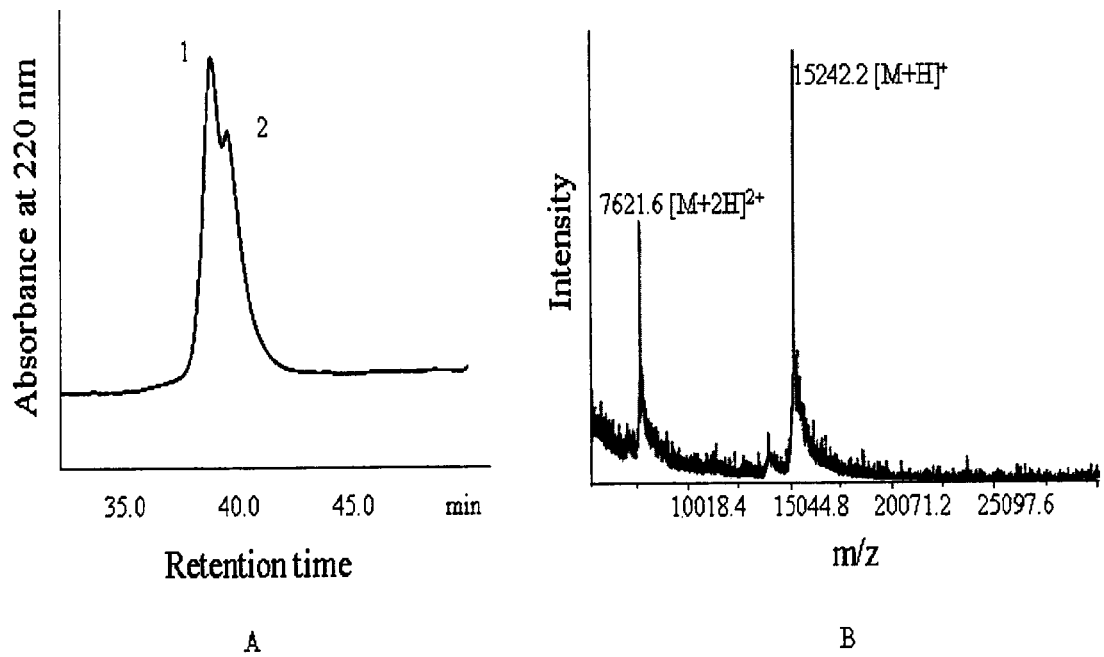
FIG. 5B. HPLC and MOLDI-MS analysis of the ligation between H3(1-13)/K4me-BMEA and H3(14-135)/K14C.
Figure 6:
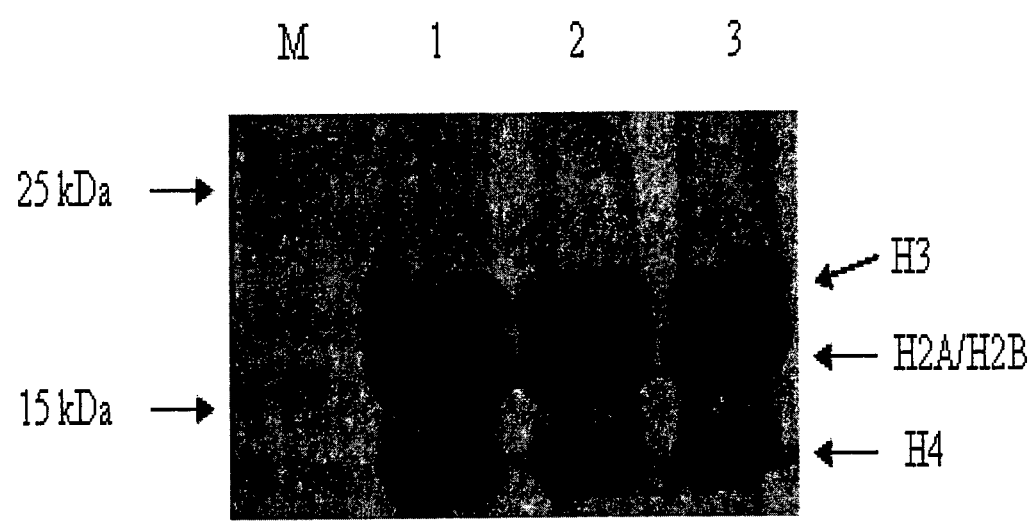
FIG. 6. 18% SDS-PAGE gel analysis of histone octamers formed from different H3 proteins. Lane 1, histone octamer with all expressed histone proteins; lane 2, with synthetic wild type H3; lane 3, with synthetic H3K4me.
Figure 7:
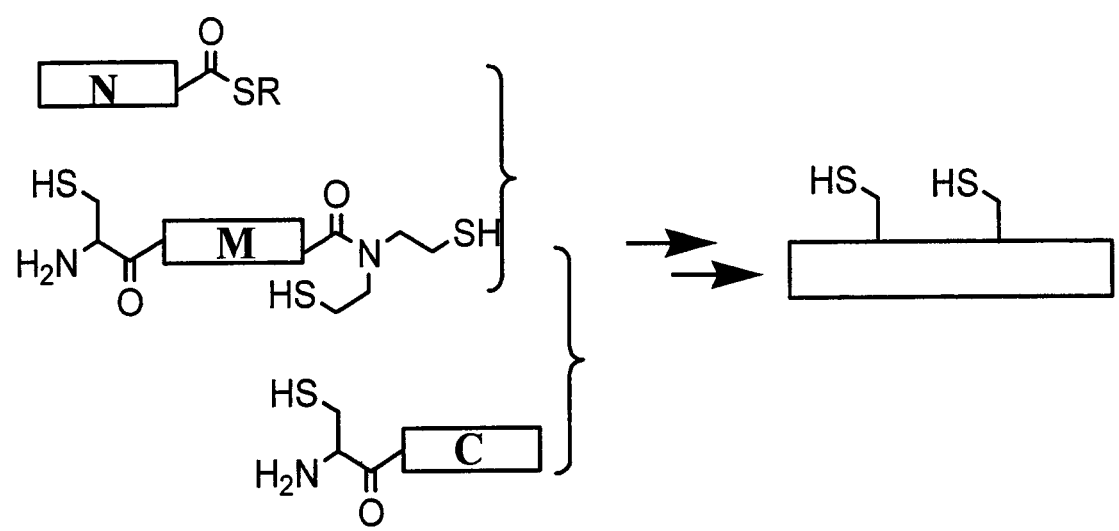
FIG. 7 illustrates our novel N-terminus to C-terminus sequential chemical ligation approach.

One can see from FIGS. 5A and 5B that, after 24 hours, more than 70% of H3(14-135)/K14C was ligated to H3(1-13) or H3(1-13)/K4me. These results indicated that the BMEA method can also be applied to the synthesis large proteins such as the histones. The synthesized H3 proteins were fully functional in their ability to form histone octamers with the other three histone proteins, H4, H2A and H2B. As seen from FIG. 6, there were no significant differences in the efficiency of octamer formation among expressed wild type H3, synthesized wild type H3, and synthesized H3 with a K4me modification. And the octamer complexes were stable in 2 M NaCl solution.

Conclusions

It has been shown that the design of the C-terminal BMEA peptides overcomes the energetic barrier of N-to-S acyl transfer to facilitate the formation of corresponding C-terminal thioesters. Although formed transiently, the thioester have a lifetime that is long enough to allow its capture for direct reaction with a cysteinyl peptide ligation partner. The reaction system is applicable to wide range of C-terminal amino acid residues, pointing to its broad utility. The successful demonstration of the synthesis of histone H3 proteins validates the practical value of the BMEA methodology in synthetic protein chemistry, which represents an important addition to the toolkit in chemical biology and protein drug discovery. Further, being very easy to use, an important advantage of the present invention is its simplicity. It is also more efficient and it allows BMEA peptides to be used directly in native chemical ligation.

Materials and Methods

Amino acids, coupling reagents and trityl resins were purchased from GL Biochem (Shanghai, China) and Novabiochem (Germany). All chemical reagents were purchased from commercial suppliers.

Synthesis of Trt-$SCH_2CH_2OH$.

1 eq. Trt-Cl in DCM was added to 1 eq. 2-mercaptoethanol in DCM with 0.1 eq. $BF_3.Et_2O$ added dropwisely. The reaction was stirred at room temperature for 1.5 hrs. The reaction mixture was quenched with water and extracted with DCM for two times. The DCM extractions were combined and washed with saturated NaCl solution. The organic phase was dried by anhydrous $Na_2SO_4$ and the solvent removed by rotary evaporation.

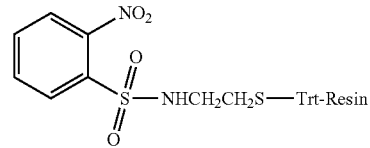

5 eq. 2-nitrobenzene-1-sulfonyl chloride and 5 eq. DIEA were dissolved in DCM/DMF and added to 1 eq. $NH_2CH_2CH_2$S-Trt-Resin in the reaction vessel. The resin mixture was shaked at room temperature for 2 hrs, followed by washing with DMF (3×) and DCM (3×).

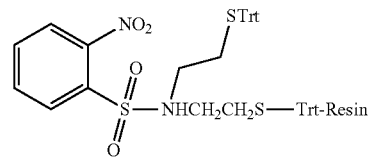

5 eq. triphenyphosphine and 5 eq. DEAD were dissolved in dry THF, then 5 eq. TrtS$CH_2CH_2$OH in dry DCM were added. The whole solution was added to the reaction vessel containing 2-nitrobenzene-1sulfonyl-NHCH$_2$CH$_2$S-Trt resin. The resin mixture was shaked at room temperature for 3 hrs, followed by washing with dry DCM (3×). This step was repeated for 2 more times.

TrtSCH$_2$CH$_2$NHCH$_2$CH$_2$S-Trt-Resin. 10 eq. DBu and 20 eq. 2-mercaptoethanol were mixed in DMF, and added to the above reaction vessel. The vessel was shaked at room temperature for overnight, followed by washing with DMF (3×) and DCM (3×).

Synthesis of BMEA peptides by Fmoc-SPPS

Attachment of the first amino acid residue 4 eq. HOAT, 4 eq. DIC and 4 eq. Fmoc amino acid (Fmoc-Gly-OH, Fmoc-Ala-OH, Fmoc-Phe-OH, Fmoc-Ser(tBu)-OH and Fmoc-Val-OH, respectively) were dissolved in dry DCM/DMF, and added to the reaction vessel. The resin mixture was shaked at room temperature for 2 hrs, followed by washing with DMF (3×) and DCM (3×).

Peptide elongation was effected using standard Fmoc SPPS protocols. The peptide was cleaved from the resin by 2% (v/v) H$_2$O, 1.5% (v/v) T is, 1.5% (v/v) 2-mercaptoethanol and 95% (v/v) TFA for 1 hr at room temperature, followed by ethyl ether precipitation. Then the crude peptide was purified by RP-HPLC.

Histone H3 Synthesis.

Construction of plasmid pET-3d-H3(14-135)/K14C overexpression system. The plasmid pET-3d containing the *Xenopus laevis* histone H3 gene was the source of the target gene. The wild type *Xenopus laevis* histone H3 gene was first mutated at Cys110 to Ala by a QuickChange Site-Directed Mutagenesis Kit (Stratagene), using a forward primer 5'-GAG GAC ACC AAC CTG GCC GCC ATC CAC GCC AAG-3' (SEQ ID NO:13) and a reverse primer 5'-CTT GGC GTG GAT GGC GGC CAG GTT GGT GTC CTC-3' (SEQ ID NO:14). The condition used was 95° C., 30 s, 18 cycles of 95° C., 30 s, 55° C., 1 min, and 68° C., 6 min. The mutated gene was transformed into XL1-Blue CaCl$_2$ competent cell (Stratagene), and amplified. Amplified plasmid pET-3d-H3/C110A, referred to as the wild type here, was purified by a plasmid purification kit (Qiagen) and the second mutation was performed based on pET-3a-H3/C110A to delete amino acid residues 1-13. The forward and reverse primers for the second mutation were: 5'-CTT TAA GAA GGA GAT ATA CAT ATG TGC GCT CCC CGC AAG CAG CTG GCC ACC-3' (SEQ ID NO:15) and 5'-GGT GGC CAG CTG CTT GCG GGG AGC GCA CAT ATG TAT ATC TCC TTC TTA AAG-3' (SEQ ID NO:16), respectively. The mutagenesis condition was the same as for the first mutation. The mutated gene was transformed into CaCl$_2$-competent BL21(DE3) pLysS cell (Stratagene).

Overexpression and purification of recombinant Histone H3(14-135)/K14C. Cells were grown in 2×TY medium containing 16 g Bacto Tryptone, 10 g yeast extract, 10 g NaCl, 100 mg ampicillin, 25 mg chloramphenicol in 1 L. After OD$_{600\,nm}$ of the cells reached 0.6-0.8, IPTG (isopropyl-β-D-thiogalactopyranoside) was added to a final concentration of 0.5 mM, and the culture was incubated for another 2 h. Cultured cells were harvested by centrifugation (Beckman centrifuge, JA-10 rotor) at 6000 rpm for 10 min at room temperature. The cells were suspended in the wash buffer (20 mM phosphate, pH 7.0, 0.5 M NaCl, 1 mM EDTA), and stored at −20° C.

The cell suspension was thawed in a water bath at 37° C. The cell lysate was sheared by a microfluider. The crude cell extract was centrifuged at 20,000×g and 4° C. for 30 min (HERMLE, Z36HK, Germany). The pellet was washed by resuspension and centrifugation twice in the wash buffer containing 0.5% (v/v) Triton X-100 to remove any cell debris and impurities. The detergent was removed by one more washing with the wash buffer. The remaining pellet was then dissolved in 6 M Gdn-HCl in the wash buffer for 1 hour at room temperature. After centrifugation to remove all the insoluble material, the supernatant was purified by C18 prep RP-HPLC using a gradient of 0%-50% for 25 min, then to 80% for 40 min of buffer B (90% ACN/0.05% TFA) in buffer A (0.05% TFA/H$_2$O) at a flowrate of 10 mL/min. The purified protein was lyophilized and molecular weight was determined by MALDI-MS.

Expression and purification of recombinant histone proteins (wild type). The plasmids pET-3a containing the *Xenopus laevis* histone H2A, H$_2$B and H4 gene and pET-3d containing H3 gene were got from Dr. C. A. Davey's lab. The plasmids were transformed into *E. coli* strain BL21(DE3)/pLysS CaCl$_2$-competent cells. Cells were grown in 2×TY medium containing 16 g Bacto Tryptone, 10 g yeast extract, 10 g NaCl, 100 mg ampicillin, 25 mg chloramphenicol in 1 L. The induction by 0.5 mM IPTG was at OD$_{600\,nm}$=0.6-0.8. The induction was for 3 h at 37° C. Cells were harvested by centrifugation at 6000×g for 10 min at room temperature. The cell pellet were suspended in the wash buffer (20 mM phosphate buffer, pH 7.0, 0.5 M NaCl, 1 mM EDTA), and stored in −20° C. The histone proteins were extracted and purified in the same way as for the truncated histone H3(14-135)/K14C (see section 8.2).

Histone octamer formation and purification. The four histones with equal molar amount (around 1 mg each) were individually dissolved in the unfolding buffer (7 M Gdn-HCl, 10 mM Tris-HCl, pH 7.5, 10 mM DTT) to a final concentration of 2 mg/mL. For histone protein H3, 20 mM DTT should be added. After 30 min unfolding, the four proteins were mixed together. The mixed solution was dialyzed against 600 mL of refolding buffer (2 M NaCl, 10 mM Tris-HCl, pH 7.5, 1 mM Na-EDTA, 10 mM 2-mercaptoethanol) at 4° C. The dialysis was done for three times, at least 4 h for each time. The precipitated material formed during dialysis was removed by centrifugation at 20,000 g for 10 min at room temperature. The supernatants was concentrated by Amicon concentrator (MW cut-off of 10 kDa) and purified by size-exclusion chromatography using the 26/60 Sephacryl S-200 column which was previously equilibrated with refolding buffer. The fractions were collected and confirmed by 18% SDS-PAGE. The purified octamer solution was mixed with equivolume glycerol, and stored at −20° C.

Example 2

Attributed to the development of solid-phase peptide synthesis (SPPS) and chemical ligation methods, especially the notable native chemical ligation[12], peptide and protein chemical synthesis was revolutionized and dramatically promoted the biochemical and biophysical study of proteins. For the total chemical synthesis of proteins using chemical ligation methods, due to the restriction of the length of the peptides which can be efficiently prepared by SPPS, two fragments are usually not sufficient to cover the full length of average-sized proteins. Therefore, the sequential or convergent condensation of multiple fragments is required.

In terms of sequential synthesis, it can be done either from C-terminus to N-terminus or in the reverse direction. When native chemical ligation (NCL) is used to synthesize a protein from C to N, it is required to protect the N-terminal cysteine residue of all the internal thioester fragments to prevent the undesired ligations. The protection step involves the use of protecting groups such as commonly-used t-butoxycarbonyl (T-Boc) which add a chemical side chain to the existing amino acid side chain. After the complete length of the peptide is synthesized, T-Boc will need to be removed in order to restore the original amino acid side chain. However, such a deprotection step involves the removal of T-Boc with a highly hazardous strong acid (hydrofluoric acid, hydrochloric acid, etc.) which hinders the use of T-Boc in many research laboratories.

Further, the deprotection and purification steps after each round of ligation introduce extra labors and lower the overall yield. While the ligation from C to N is straightforward, the ligation in reverse direction is more challenging. To make sure that the N to C sequential ligation works, it is required that the C-terminal moiety of middle Cys-peptide remains intact during the first ligation and therefore available for next ligation step. Based on this principle, many N to C sequential ligation methods were developed by using two or more orthogonal ligation chemistries. When NCL was used as the sole chemistry in N to C sequential ligation, the sequential ligation was either kinetically controlled by using two thioesters with different reactivity[13] or by using thioester precursors[14]. Unlike the kinetically control ligation approaches which are more straightforward, the thioester precursor approaches may require extra manipulations to convert the precursors to thioesters after each round of ligation. However, these manipulations may be performed in situ with the ligation reaction therefore to avoid the purification steps.[15]

The challenge of synthesizing peptides and proteins in an efficient, direct and rapid manner with high product yield remains. Given that the current peptide and protein synthesizing techniques do not always result in an intact product after ligation, efficiently produce high yields of protein or conveniently synthesize mid-ranged to large-sized proteins, there is a need to improve the efficacy of protein synthesis methods that overcomes, or at least ameliorates, one or more of the disadvantages described above.

Herein, we introduce a novel N to C sequential ligation approach through the combination of NCL and the peptidyl N,N-bis(2-mercaptoethyl)-amide (BMEA) mediated ligation. It has been found that peptidyl BMEA can serve as a thioester precursor. Under mild acidic conditions (pH 4-6), peptidyl BMEA can: i) be converted to thioester by exchanging the BMEA moiety with thiols; ii) ligate with Cys-peptide in situ. While under alkaline conditions, it remains in its amide form with low reactivity with cys-peptide. Based on these observations, we realize that when a peptide thioester reacts with Cys-peptidyl BMEA under alkaline condition, the NCL will be dominant and BMEA moiety will remain intact after ligation. Therefore, we propose a novel three segmental N to C sequential ligation strategy. As shown in FIG. 21, the first step is the NCL reaction between N-terminal thioester and middle Cys-peptidyl BMEA segment. The second step is the BMEA mediated ligation between the ligation product and the C-terminal Cys-peptide.

To test our proposal, we first synthesized three short model peptides. Peptide 2, the middle Cys-peptidyl BMEA segment, was synthesized as previously reported.[16] For the first ligation step, 1 and 2 was reacted with each other under normal NCL condition. 15 mM of 1 and 5 mM of 2 were dissolved in ligation buffer containing 6 M Gdn.HCl, 0.2 M phosphate, 50 mM TCEP, 2% v/v thiophenol, pH 7.0. The ligation reaction was monitored with HPLC. After 4 hours at room temperature, the reaction was completed with only minor side reactions. The ligation product was purified and subjected to next ligation step with peptide 3. The ligation was performed under the optimal condition for BMEA mediated ligation. 5 mM ligation product and 15 mM of peptide 3 were dissolved in ligation buffer containing 6 M Gdn.HCl, 0.2 M NaOAc, 50 mM TCEP, 0.2 M MESNa, pH 5.0. The ligation was completed under microwave irradiation within 15 hours. The study with model peptides has demonstrated that our N to C sequential ligation strategy works.

Peptide 1:
H-ADKRAHHNALERKRRDHA-S(CH$_2$)$_2$CONH$_2$ (SEQ ID NO: 4)

Peptide 2:
H-CDSFHSLRDSY-N(CH$_2$CH$_2$SH)$_2$ (SEQ ID NO: 5)

Peptide 3:
H-CLKPLHEKDSES($_p$)GGGKD-NH$_2$ (SEQ ID NO: 6)
S(p): phosphoserine Example 3

We applied our strategy to the synthesis of a mid-sized protein, ubiquitin. Ubiquitin is a highly conserved protein with 76 amino acids and can be linked to the lysine side chain of other ubiquitin or other proteins with its carboxlyate terminus through the process called ubiquitination. The chemical synthesis of ubiquitin has been extensively studied. Previously, Kent's group has synthesized ubiquitin through the C to N sequential ligation of three segments with Ala28Cys and Ala46Cys as ligation junctions.[17] Recently, our group also synthesized an ubiquitin derivative from C to N direction with Ala28Cys and Lys48 as ligation junctions.[18] Although the C to N synthesis of ubiquitin has been extensively studied, the N to C synthesis of ubiquitin has not been reported.

To synthesize ubiquitin with N to C sequential ligation, three segments were synthesized using SPPS. The middle Cys-Peptidyl BMEA segment 5 was synthesized using a revised approach. Briefly, 2-chlorotritryl chloride resin was treated with 30% trifluoroacetic acid (TFA) in dichloromethane (DCM) to generate tritryl carbocation. The color of the resin turned dark red. After brief wash, a solution of N,N-bis(2-mercaptoethyl)-amine.TFA salt in DCM was mixed with resin. The color of the resin immediately turned to normal yellow color which indicated the complete of the loading of linker to the resin. The loading of the amino acids was the same as previously reported.[16] The new linker synthesis method was faster and simplified compared to the previous approach.[16]

Peptide 4: (SEQ ID NO: 17)
H-LQIFVKTLTGKTITLEVEPSDTIENVK-S(CH$_2$)$_2$CONH$_2$ Peptide 5:
H-CKIQDKEGIPPDQQRLIF-N(CH$_2$CH$_2$SH)$_2$ (SEQ ID NO: 18)

Peptide 6:
H-CGKQLEDGRTLSDYNIQKESTLHLVLRLRGG-OH (SEQ ID NO: 19)

For the first NCL step, 3.5 mg (3.8 mM) of the N-terminal peptide thioester 4 and 2.3 mg (3.4 mM) of the middle segment 5 were dissolved in 300 µl, of ligation buffer containing 6 M Gdn.HCl, 0.2 M phosphate, 20 mM TCEP and 0.2 M MESNa, pH 8.0. As shown in FIG. 15A, the ligation was completed within 5 hours at room temperature. No side reactions derived from BMEA moiety were observed. Further incubation for 1.5 hours, no change in the HPLC profile was observed which indicated that the BMEA moeity was stable under the ligation condition. After purification and lyophilization, 2.5 mg of ligation product H-LF$_{45}$-BMEA was isolated.

For the second step of ligation, we had two options. (FIG. 21). We can either convert the peptidyl BMEA to thioester and perform the NCL between isolated thioester and the C-terminal cys-peptide or let the peptidyl BMEA directly react with the cys-peptide. Note that when the first option is used this N—C sequential ligation can, in principle, be performed for infinite steps if the BMEA is converted to an isolated thioester at every intermediate step.

We first explored the first option for the second step of ligation. To convert H-LF$_{45}$-BMEA to thioester, about 3 mg of H-LF$_{45}$-BMEA was dissolved in 300 μl, buffer (containing 6 M Gdn.HCl, 0.2 M NaOAc, 0.2 M MESNa, 40 mM TCEP, pH 5.0) and irradiated with low-power microwave. After 10 h, majority of the BMEA was converted to the thioester form with small amount of hydrolysis product (FIG. 16). 1.5 mg of H-LF$_{45}$-MES was isolated after HPLC purification.

Next, H-LF$_{45}$-MES was reacted with peptide 6 under NCL condition. 1.5 mg of H-LF$_{45}$-MES and 1.5 mg of 6 were dissolved in 200 μL NCL buffer (6 M Gdn.HCl, 0.2 M phosphate, 20 mM TCEP and 0.2 M MESNa, pH 8.0). The reaction was completed within 6 hours (FIG. 17). 1.4 mg of ligation product was isolated.

We then tested the ligation between H-LF$_{45}$-BMEA and 6 in situ. The reaction underwent under microwave irradiation at pH 5.0. We first used MESNa as the thiol additive and found that when lower ratio of 6 (1.5 to 2 equivalent) relative to H-LF$_{45}$-BMEA was used, the ligation was less efficient. After 5 hour irradiation, all H-LF$_{45}$-BMEA was transformed to H-LF$_{45}$-MES. But only 30% to 40% of the thioester reacted with 6 and formed the ligation product. Continuing irradiation could not increase the yield (Data not shown). The ligation reaction was more efficient when larger excess (about 3 equivalent) of 6 was used. After microwave irradiation for 10 hours, more than 70% of H-LF$_{45}$-MES was converted to ligation product. (FIG. 18).

Based on our observations, we realized that MESNa might not be a good thiol additive for BMEA mediated ligation when very long peptide segments were involved. Although aromatic thiols have been shown to be effective additives for NCL, they might not be suitable for our case because: i) they have strong absorption at 220 nm and their retention time may be very close to those long peptide segments; ii) they may have poor solubility under acid condition. Taking into the account of these considerations, we tested another alkyl thiol, methyl mercaptoacetate, as the thiol additive. 1 mg (1.9 mM) of H-LF$_{45}$-BMEA and 1.4 mg (4 mM) of 6 were dissolved in 100 μL buffer (6 M Gdn.HCl, 0.2 M NaOAc, 2% v/v methyl mercaptoacetate, 40 mM TCEP, pH 5.0). The reaction was completed after microwave irradiation for 7 hours (FIG. 15C). Almost all the H-LF$_{45}$-BMEA was consumed and ligated with peptide 6. Compared with MESNa, when methyl mercaptoacetate served as thiol additive, the ligation between H-LF$_{45}$-BMEA and 6 was much more efficient.

To generate the native sequence of ubiquitin, free radical mediated desulfurization[19] was performed with the full length ubiquitin synthesized by our N to C sequential ligation approach to convert the two cysteine residues at the ligation junctions to alanine. The desulfurization process was monitored with analytic HPLC and ESI-MS. The desulfurization was completed within 8 hours (FIG. 19). The end product was purified by C18 semi-preparative HPLC. Next, the chemically synthesized ubiquitin was refolded through dialysis. Circular dichroism (CD) was measure to confirm that the protein has been refolded to its native state. (FIG. 20).

In summary, we have demonstrated that the chemical synthesis of proteins can be achieved from N-terminus to C-terminus through the combinatal use of native chemical ligation and BMEA mediated ligation. For the BMEA mediated ligation step, we also explored the different options: i) ligation with isolated thioester or direct ligation in situ; ii) different thiol additives. Our methodology does not only work for small peptides also efficient when long peptides segments are involved. In addition, we also revised and optimized the strategy for the synthesis of peptidyl BMEA. The new strategy was simple, time-saving and suitable for the synthesis of longer peptide BMEA segment. With these efforts, we believe that the newly developed N to C sequential ligation strategy has great value in protein synthesis.

Supporting Information to Examples 2 and 3
General Methods.

Amino acid derivatives, coupling reagents and resins were purchased from Novabiochem and GL Biochem (Shanghai, China). All the other chemical reagents were purchased from Alfa Aesar, Sigma-Aldrich Chemical Company, Fisher Scientific, and Acros Organics. All the analytical HPLC analyses were performed using a Shimadzu HPLC system equipped with a Jupiter C18 (5 um, 4.6×250 mm) reverse-phase column with a flow rate of 1.0 mL/min. Detection was done with a UV-VIS-detector at 220 nm. The purification was performed using a semi-preparative HPLC column (Jupiter C18, 5 um, 10×250 mm) on a Shimadzu system with a flow rate of 2.5 mL/min. The buffer system for all the analyses was buffer A—H$_2$O (containing 0.045% TFA) and buffer B—90% acetonitrile in H$_2$O (containing 0.045% TFA). Peptide and protein masses were measured using a Thermo FINNIGAN LCQ Deca XP MAX equipped with ESI ion source or a 4800 MALDI TOF/TOF Analyzer with α-cyano-4-hydroxycinnamic acid as the matrix.

Solid Phase Peptide Synthesis:
Synthesis of Thioester Peptides.

H-ADKRAHHNALERKRRDHA-SCH$_2$CH$_2$CONH$_2$ (Peptide 1) (SEQ ID NO:4) and Ubiquitin L1-K27-SCH$_2$CH$_2$CONH$_2$ (peptide 4) were manually synthesized employing standard t-Boc chemistry. First, Trt-SCH$_2$CH$_2$COOH was coupled onto MBHA resin. The trityl group was removed by treatment with a cocktail containing TFA/TIS/β-mercaptoethanol/DCM (5:2.5:2.5:90). For the coupling of amino acids, Boc-amino acid (4 eq.) and benzotriazol-1-yl-oxytripyrrolidinophosphonium hexafluorophosphate (PyBOP) (4 eq.) were dissolved in DCM. DIEA (12 eq.) was added in the solution. After 2 min of activation, the mixture was mixed with resin. The reaction was undertaken for 1.5 h. The coupling efficiency was checked with Kaiser test. The Boc group was removed by treatment with 30% TFA in DCM for 10 min, followed by 15 min. The side chain protected amino acid derivatives used were Boc-Asp(OBzl)-OH, Boc-Lys(2-Cl-Z)-OH, Boc-Arg(Tos)-OH, Boc-His (Tos)-OH, Boc-Asn(Xan)-OH, Boc-Glu(OBzl)-OH, Boc-Gln(Xan)-OH, Boc-Thr(Bzl)-OH, Boc-Ser(Bzl)-OH. After sequence assembly, peptide 1 was cleaved from the resin with a cocktail consisting TFMSA/TFA/p-cresol/methyl phenyl sulfide (1:7:1:1) for 1 h. Peptide 4 was cleaved from the resin with HF/p-cresol (9:1) at 0° C. for 1.5 h. The crude peptides were precipitated with cold ether and purified with C18 semi-preparative HPLC.

Synthesis of Peptidyl BMEA.

Peptide H-CDSFHSLRDSY-N(CH$_2$CH$_2$SH)$_2$ (peptide 2) (SEQ ID NO:5) was synthesized as previously described. Briefly, cysteamine was first loaded to 2-chlorotrityl chloride resin. The amino group was protected with 2-nitrobenzenesulfonyl chloride. The Mitsunobu reaction was then performed. 5 eq. triphenylphosphine and 5 eq. of DEAD were dissolved in dry THF, and then 5 eq. of TrtSCH$_2$CH$_2$OH in dry DCM was added. The whole solution was added to the resin. The resin was incubated at room temperature for 3×3 h. The 2-nitrobenzenesulfonyl group was then removed by overnight treatment with 10 eq. of DBU and 20 eq. of 2-mercaptoethanol in DMF. The first amino acid was loaded with 4 eq. of DIC, 4 eq. of HOAt and 4 eq. of Fmoc-AA-OH in dry DCM/DMF. The coupling of the remaining amino acids was done using the standard Fmoc chemistry with PyBOP as the coupling reagent. For the synthesis of ubiquitin H-C28-F45-N(CH$_2$CH$_2$SH)$_2$ (peptide 5), the N,N-bis(2-mercaptoethyl)-amine was directly loaded onto 2-chlorotrityl chloride resin. 1 gram resin (1.3 mmol/g) was treated with 30% TFA in DCM for 5 min and washed with dry DCM for 3 times. The resin turned dark red or black. The solution of 1.5 mmole N,N-bis(2-mercaptoethyl)-amine.TFA salt in dry DCM was mixed with resin. After a few minutes, the resin turned to the normal yellow color which indicated the completion of the loading. The resin was washed with DCM and DMF. The Ellman's test was positive indicating the presence of unattached thiol group. The small amount of the unattached thiol group was protected with 100 µL of S-methyl mathanethiosulfonate (MMTS) and 100 µL of DIEA in DMF for 20 min. The coupling of the amino acids was the same as synthesis of peptide 2. After synthesis, the peptides were cleaved from resin with a mixture containing 95% TFA, 1.5% EDT, 1.5% TIS and 2% H$_2$O for 1 h or 3 h (if Arg was present). The crude peptide was precipitated with cold ether and purified with semi-preparative HPLC.

Synthesis of C-Terminal Cys-Peptides.

The peptide H-CLKPLHEKDSES($_p$)GGGKD-NH$_2$ (peptide 3) (SEQ ID NO:6) and the ubiquitin H-C46-G76-OH (peptide 6) were synthesized using the standard Fmoc chemistry. Rink amide MBHA resin (0.65 mmol/g) was used for the synthesis of peptide 3. First, the Fmoc group was removed with 20% piperidine in DMF for 2 min, followed by 20 min. For the coupling reaction, 4 eq. of Fmoc-AA-OH, 4 eq. of PyBOP and 8 eq. of DIEA were dissolved in DMF. After preactivation for 2 min, the mixture was added to the resin. The coupling reaction was performed for 1.5 to 2 hours. The Fmoc amino acids used were Fmoc-Cys(Trt)-OH, Fmoc-Lys(Boc), Fmoc-His(Trt)-OH, Fmoc-Glu(OtBu)-OH, Fmoc-Asp(OtBu)-OH, Fmoc-Ser(tBu)-OH. Fmoc-Ser(Phosphory)-OH was used for the installation of phosphorylated serine. Peptide 6 was synthesized using Wang resin (0.44 mmol/g). The C-terminal Gly was loaded by using 8 eq. DCC, 0.8 eq DMAP, 8 eq. Fmoc-Gly-OH in dry DCM/DMF overnight. The loading was repeated for another 5 h and the resin was then capped with Ac$_2$O for 1 h. Fmoc group was removed with 20% piperidine in DMF. The following amino acids were coupled using 4 eq. PyBOP, 4. eq. amino acid, 8 eq. DIEA preactivated in DMF. On average, each coupling reaction lasted for 1.5 h. The coupling was monitored with ninhydrin test. The Nα-Fmoc protected amino acids used were Fmoc-Arg(Pbf)-OH, Fmoc-His(Trt)-OH, Fmoc-Thr(tBu)-OH, Fmoc-Ser(tBu)-OH, Fmoc-Glu(OtBu)-OH, Fmoc-Lys(Boc)-OH, Fmoc-Gln(Trt)-OH, Fmoc-Asn(Trt)-OH, Fmoc-Tyr(tBu)-OH, Fmoc-Asp(OtBu)-OH, Fmoc-Cys(Trt)-OH. The Gly at the AspGly junction was coupled using Fmoc-(Hmb)Gly-OH (2 eq. PyBOP, 2 eq. amino acid, 4 eq. DIEA). After sequence assembly, the resin was treated with 20% piperidine in DMF for 20 min to remove Fmoc group and hydrolyze any possible acylation at hydroxyl group of Hmb group of (Hmb)Gly residue. The resin was then cleaved with TFA/TIS/H2O/EDT (92.5/2.5/2.5/2.5) for 2.5 h. The crude peptide was precipitated with cold ether and purified with C18 preparative HPLC. The desired product was analyzed with C18 analytic HPLC and ESI-MS.

Free Radical Mediated Desulfurization:

The desulfurization was performed under N$_2$. All the solutions were prepared under N$_2$ immediately before use. 1.5 mg of sulfur containing ubiquitin was dissolved in 300 µL buffer containing 6 M Gdn.HCl, 0.1 M phosphate, pH 6.5. 50 µL of 1 M TCEP solution (neutralized with 5 M NaOH) was added. 25 µL of 10 mM glutathione was added. 20 µL of 0.2 M VA-044 was added. The solution was stirred at 37° C. 5 h. 10 µL of 0.2 M VA-044 was added to the mixture and the solution was continuously stirred for another 3 h. The desulfurization reaction was analyzed with C18 analytic HPLC (FIG. 19). The final diubiquitin was purified by C18 semi-preparative HPLC and lyophilized. 1.1 mg of final product was isolated.

Circular Dichroism (CD) Measurement of Refolded Ubiquitin:

For the folding of ubiquitin, 1.1 mg of desulfurized ubiquitin was dissolved in 0.2 mL buffer (6 M Gdn.HCl, 10 mM phosphate, 100 mM NaCl, pH 7.4) and dialyzed against water. After refolding, the CD of ubiquitin was measured with Chirascan spectrometer with the final dialysis solution as baseline. The scan was performed between 180-260 nm and the passlength was 1 mm.

Example 4

Homologues of BMEA Peptide

BMEA peptides can undergo the N to S acyl transfer through a five-membered ring intermediate. We investigated whether similar compounds can also undergo the N to S acyl transfer through a six-membered ring intermediate. So we designed two systems, peptide LKSFG-N(CH$_2$CH$_2$SH, CH$_2$CH$_2$CH$_2$SH) (SEQ ID NO:12) and peptide LKSFG-N(CH$_2$CH$_2$CH$_2$SH)$_2$. (SEQ ID NO:10).

1 Synthesis of Peptide LKSFG-N(CH$_2$CH$_2$SH, CH$_2$CH$_2$CH$_2$SH) (SEQ ID NO:12) and LKSFG-N(CH$_2$CH$_2$CH$_2$SH)$_2$ (SEQ ID NO:10).

TrtSCH$_2$CH$_2$CH$_2$NCH$_2$CH$_2$S-(2-chloro)trityl resin was prepared in almost the same way as for BMEA trityl resin except that TrtSCH$_2$CH$_2$CH$_2$OH was added to

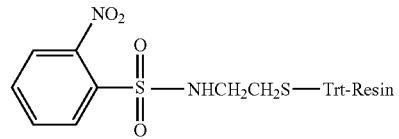

in the Mitsunobu reaction. After removal of the sulfonyl group, amino acid were coupled to the resin by standard Fmoc SPPS. The ESI-MS and analytical RP-HPLC spectra of peptide LKSFG-N(CH$_2$CH$_2$SH, CH$_2$CH$_2$CH$_2$SH) (SEQ ID NO:12) were shown below in FIG. 22 below. Interestingly, two small peaks (peak 2 and peak 3 in FIG. 22) were observed which corresponded to the two thioesters after N to S acyl transfer. One is LKSFG-SCH$_2$CH$_2$NHCH$_2$CH$_2$CH$_2$SH, (SEQ ID NO:20) and the other is LKSFG-SCH$_2$CH$_2$CH$_2$NHCH$_2$CH$_2$SH (SEQ ID NO:21).

Similarly LKSFG-N(CH$_2$CH$_2$CH$_2$SH)$_2$ (SEQ ID NO:10) was also prepared. The ESI-MS and analytical RP-HPLC spectra of peptide LKSFG-N(CH$_2$CH$_2$CH$_2$SH)$_2$ (SEQ ID NO:10) were as shown in FIG. 23.

2 Ligation of Peptide LKSFG-N(CH$_2$CH$_2$SH, CH$_2$CH$_2$CH$_2$SH) (SEQ ID NO:12) or peptide LKSFG-N(CH$_2$CH$_2$CH$_2$SH)$_2$ (SEQ ID NO:10) Respectively with Peptide CLKFA-Amide Identical ligation conditions were used, i.e., 15 mM CLKFA, 100 mM acetate buffer pH 5, 50 mM TCEP and 1% (v/v) benzylmercaptan at 37° C., for 5 mM LKSFG-BMEA (SEQ ID NO:3), LKSFG-N(CH$_2$CH$_2$SH, CH$_2$CH$_2$CH$_2$SH) (SEQ ID NO:12) or peptide LKSFG-N(CH$_2$CH$_2$CH$_2$SH)$_2$, (SEQ ID NO:10) respectively. The reaction status was monitored by HPLC at 2 h, 4 h, 8 h and 24 h (see FIG. 24).

The reaction rate of peptide H-LKSFG-N(CH$_2$CH$_2$SH, CH$_2$CH$_2$CH$_2$SH) (SEQ ID NO:12) was slightly faster than that of LKSFG-BMEA (SEQ ID NO:3) (FIGS. 24A&B) under the same conditions. No side reactions were detected and the molecular mass of ligation product was confirmed by ESI-MS. However, the reaction rate of peptide LKSFG-N(CH$_2$CH$_2$CH$_2$SH)$_2$ (SEQ ID NO:10) was much slower than that of LKSFG-BMEA (SEQ ID NO:3) (FIGS. 24A&C), but the reaction underwent cleanly with no detectable side reactions. It is not completely clear as to why there is such a dramatic decrease in reactivity with the bis(2-mercaptopropyl)amides. One possible explanation is that the amide becomes less active as the sulfur is farther away from it. Another possible reason is that a six-membered ring intermediate is less likely to form than a five-membered ring system.

REFERENCES (1) (a) Aimoto, S. *Biopolymers* 1999, 51, 247-265. (b) Dawson, P. E.; Kent, S. B. H. *Annu. Rev. Biochem.* 2000, 69, 923. (c) Tam, J. P.; Yu, Q.; Miao, Z. *Biopolymers* 1999, 51, 311. (d) Kent, S. B. H. *Chem. Soc. Rev.* 2009, 38, 338.
(2) Dawson, P. E.; Muir, T. W.; Clark-Lewis, I.; Kent, S. B. H. *Science* 1994, 266, 776.
(3) For recent reviews, see: (a) Hackenberger, C. P. R.; Schwarzer, D. Angew. Chem. Int. Ed. 2008, 47, 10030-10074. (b) Kang, J.; Macmillan, D. *Org. Biomol. Chem.* 2010, 8, 1993-2002.
(4) (a) Tam, J. P.; Lu, Y.-A.; Liu, C.-F.; Shao, J. *Proc. Natl. Acad. Sci. U.S.A.* 1995, 92, 12485. (b) Hackeng, T. M.; Giffin, J. H.; Dawson, P. E. *Proc. Natl. Acad. Sci. U.S.A.* 1999, 96, 10068-10073.
(5) Li, X.; Kawakami, T.; Aimoto, S. *Tetrahedron Lett.* 1997, 38, 6237-6240.
(6). (a) Shin, Y.; Winans, K. A.; Backes, B. J.; Kent, S. B. H.; Ellman, J. A.; Bertozzi, C. R. J. Am. Chem. Soc. 1999, 121, 11684-11689. (b) Ingenito, R.; Bianchi, E.; Fattori, D.; Pessi, A. J. Am. Chem. Soc. 1999, 121, 11369-11374. (c) Mende, F.; Seitz, O. Angew. Chem., Int. Ed. 2007, 46, 4577-4580. (d) Blanco-Canosa, J. B.; Dawson, P. E. *Angew. Chem., Int. Ed.* 2008, 47, 6851-6855. (e) Tofteng, A. P.; Sørensen, K. K.; Conde-Frieboes, K. W.; Hoeg-Jensen, T.; Jensen, K. J. *Angew. Chem., Int. Ed.* 2009, 48, 7411-7414.
(7) (a) Warren, J. D.; Miller, J. S.; Keding, S. J.; Danishefsky, S. J. J. Am. Chem. Soc. 2004, 126, 6576-6578. (b) Botti, P.; Villain, M.; Manganiello, S.; Gaertner, H. Org. Lett. 2004, 6, 4861-4864. (c) Tan, X.-H.; Wirjo, A.; Liu, C.-F. Chembiochem 2007, 8, 1512-1515.
(8) (a) Futaki, S.; Sogawa, K.; Maruyama, J.; Asahara, T.; Niwa, M.; Hojo, H. Tetrahedron Lett. 1997, 38, 6237-6240. (b) Alsina, J.; Yokumu, T. S.; Albericio, F.; Barany, G. J. Org. Chem. 1999, 64, 8761-8769. (c) Swinnen, D.; Hilvert, D. Org. Lett. 2000, 2, 2439-2442. (d) Brask, J.; Albericio, F.; Jensen, K. J. *Org. Lett.* 2003, 5, 2951.
(e) von Eggelkraut-Gottanka, R.; Klose, A.; Beck-Sickinger, A. G.; Beyermann, M. *Tetrahedron Lett.*, 2003, 44, 3551. (f) Hackenberger, C. P. R.; Friel, C. T.; Radford, S. E.; Imperiali, B. *J. Am. Chem. Soc.* 2005, 127, 12882. (g) T. Murase, T. Tsuji and Y. Kajihara, *Carbohydr. Res.*, 2009, 344, 762. (h) A. P. Tofteng, K. S. Kasper, W. C.-F. Kilian, H.-J. Thomas and J. J. Knud, *Angew. Chem., Int. Ed.* 2009, 48, 7411.
(9) (a) Kawakami, T.; Sumida, M.; Nakamura, K.; Vorherr, T.; Aimoto, S. Peptide thioester preparation based on an N→S acyl shift reaction mediated by a thiol ligation auxiliary. *Tetrahedron Lett.* 2005, 46, 8805-7. (b) Ollivier, N.; Behr, J.-B.; El-Mandi, O.; Blanpain, A.; Melnyk, O. *Org. Lett.* 2005, 7, 2647-2650.
(c) Nagaike, F.; Onuma, Y.; Kanazawa, C.; Hojo, H.; Ueki, A.; Nakahara, Y.; Nakahara, Y. *Org. Lett.* 2006, 8, 4465-4468. (d) Hojo, H.; Onuma, Y.; Akimoto, Y.; Nakahara, Y.; Nakahara, Y. *Tetrahedron Lett.* 2007, 48, 25-28. (e) Ohta, Y.; Itoh, S.; Shigenaga, A.; Shintaku, S.; Fujii, N.; Otaka, A. *Org. Lett.* 2006, 8, 467-470. (f) Tsuda, S.; Shigenaga, A.; Bando, K.; Otaka, A. N→S Acyl-Transfer-Mediated Synthesis of Peptide Thioesters Using Anilide Derivatives. *Org. Lett.* 2009, 11, 823-826.
(10) (a) Kawakami, T.; Aimoto, S. *Tetrahedron Lett.* 2007, 48, 1903-1905. (b) Kang, J.; Reynolds, N. L.; Tyrrell, C.; Dorin, J. R.; Macmillan, D. *Org. Biomol. Chem.* 2009, 7, 4918.
(11) (a) Chong, S.; Mersha, F. B.; Comb, D. G.; Scott, M. E.; Landry, D.; Vence, L. M.; Perler, F. B.; Benner, J.; Kucera, R. B.; Hirvonen, C. A.; Pelletier, J. J.; Paulus, H.; Xu, M.-Q. *Gene* 1997, 192, 271-281. (b) Evans, T. C.; Xu, M. Q. Chem. Rev. 2002, 102, 4869-4884. (c) Muir, T. W. Annu. Rev. Biochem. 2003, 72, 249-289.
(12) Dawson, P. E.; Muir, T. W.; Clark-Lewis, I.; Kent, S. B. H. Science 1994, 266, 776.
(13) (a) Tan, X.-H.; Zhang, X; Yang, R; Liu, C.-F. *Chem Biochem* 2008, 9, 1052. (b) Li, X.; Lam, H. Y.; Zhang, Y.; Chan, C. K. *Org. Lett.* 2010, 12, 1724.
(14) (a) Bang, D.; Pentelute, B. L.; Kent, S. B. H. *Angew. Chem., Int. Ed.* 2006, 45, 3985. (b) Zheng, J. S.; Cui, H.-K.; Fang, G.-M.; Xi, W.-X.; Liu, L. *Chem Biochem* 2006, 7, 429.
(15) (a) Kawakami, T.; Aimoto, S. *Tetrahedron Lett.* 2007, 48, 1903. (b) Shigenaga, A.; Sumikawa, Y.; Tsuda, S.; Sato, K.; Otaka, A. *Tetrahedron* 2010, 66, 3290.
(16) Hou, W.; Zhang, X.; Li, F.; Liu, C.-F. *Org. Lett.* 2011, 13, 386.
(17) Bang, D.; Makhatadze, G. I.; Tereshko, V.; Kossiakoff, A. A.; Kent, S. B. H. *Angew. Chem., Int. Ed.* 2005, 44, 3852.
(18) Yang, R.; Pasunooti, K. K.; Li, F.; Liu, X.-W.; Liu, C.-F. *Chem. Commun.* 2010, 46, 7199.
(19) Wan, Q.; Danishefsky, S. J. *Angew. Chem., Int. Ed.* 2007, 46, 9248.

The invention claimed is:

1. A method of peptide synthesis comprising a step of reacting a compound to form a polypeptide or protein, the compound having the following structural formula:

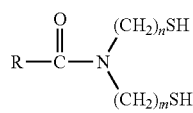

wherein
n is 2 or 3;
m is 2 or 3;
and RC(O)— is an amino acyl or peptidyl group, or R is selected from the group consisting of hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$.

2. A method of peptide synthesis comprising the step of reacting a resin of formula:

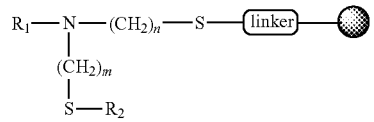

wherein represents a resin or solid support;

n is 2 or 3;
m is 2 or 3;
R$_1$ is H or Fmoc;
R$_2$ is H or a protecting group; and
"linker" is any linker compatible with Fmoc chemistry.

3. The method of claim 2, wherein the resin is of formula:

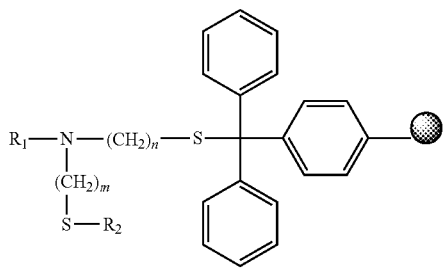

wherein R$_2$ is trityl.

4. The method of claim 2, wherein the peptide comprises a C-terminal tertiary N,N-bis(2-mercaptoethyl)-amide group; N-(2-mercaptoethyl)-N-(3-aminopropyl)-amide group or N,N-bis(3-mercaptopropyl)-amide.

5. The method of claim 2, further comprising a step of reacting a thiol additive selected from the group consisting of an alkyl thiol, benzyl mercaptan, MESNa, and methyl mercaptoacetate.

6. The method of claim 2, comprising an Fmoc solid-phase peptide synthesis.

7. The method of claim 2, wherein the product of the method of peptide synthesis is a polypeptide or protein.

8. A method of thioester peptide synthesis comprising the steps of reacting a compound of formula:

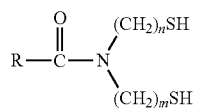

with a thiol-containing compound R'SH in the presence of a protic acid, thereby forming a thioester compound of formula:

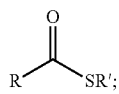

wherein
n is 2 or 3;
m is 2 or 3;
and RC(O)— is an amino acyl or peptidyl group, or R is selected from the group consisting of hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$.

9. The method of claim 8, wherein the thiol-containing compound R'SH is selected from the group consisting of 3-mercaptopropionic acid, benzylmercaptan, methyl mercaptoacetate, and MESNa.

10. A method comprising steps of:
(i) reacting a resin of formula (A):

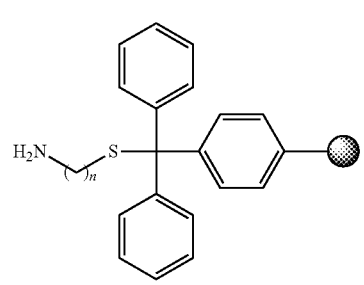

with o-NO$_2$PhSO$_2$—Cl, DIEA, and CH$_2$Cl$_2$-DMF to obtain a resin of formula (B):

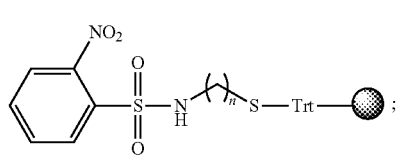

(ii) alkylating the resin of formula (B); and
(iii) removing the sulfonyl group thiolytically;
thereby producing a resin of formula (C):

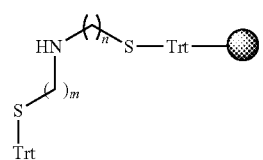

wherein:
Trt is trityl;
n is 2 or 3; and
m is 2 or 3.

11. The method of claim 10, further comprising steps of:
(iv) performing Fmoc solid phase peptide synthesis on the resin of formula (C); and
(v) cleaving from the resin to produce a compound of formula (D):

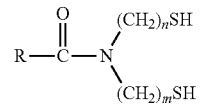

wherein
n is 2 or 3;
m is 2 or 3; and and RC(O)— is an amino acyl or peptidyl group, or R is selected from the group consisting of hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$.

12. The method of claim 8, wherein:
i) n is 2, and m is 2; or
ii) n is 2, and m is 3; or
iii) n is 3, and m is 2.

13. The method of claim 11, wherein:
i) n is 2, and m is 2; or
ii) n is 2, and m is 3; or
iii) n is 3, and m is 2.

14. The method of claim 1, wherein in place of a N,N-bis (2-mercaptoethyl) (BMEA) moiety a BMEA variant is used in which cysteine replaces a mercaptoethylamine, wherein the structure of the BMEA variant is

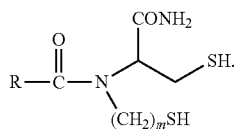

15. The method of claim 2, wherein in place of a N,N-bis (2-mercaptoethyl)-amide (BMEA) moiety a BMEA variant is used in which cysteine replaces a mercaptoethylamine wherein the structure of the BMEA variant is

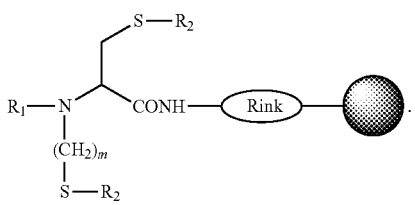

16. The method of claim 8, wherein in place of a N,N-bis (2-mercaptoethyl)-amide (BMEA) moiety a BMEA variant is used in which cysteine replaces a mercaptoethylamine wherein the structure of the BMEA variant is

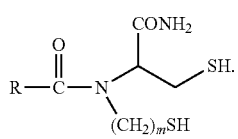

17. The method of claim 10, wherein in place of a N,N-bis (2-mercaptoethyl)-amide (BMEA) moiety a BMEA variant is used in which cysteine replaces a mercaptoethylamine wherein the structure of the BMEA variant is

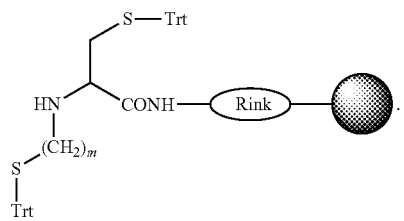

18. The method of claim 1, wherein the method is conducted at a pH of between 4 and 6.

19. The method of claim 1, wherein the method comprises the step of applying microwave radiation.

20. The method of claim 2, wherein the method is conducted at a pH of between 4 and 6.

21. The method of claim 2, wherein the method comprises the step of applying microwave radiation.

22. The method of claim 8, wherein the method is conducted at a pH of between 4 and 6.

23. The method of claim 8, wherein the method comprises the step of applying microwave radiation.

24. A method of peptide synthesis comprising a step of reacting a compound to form a polypeptide or protein, the compound having the following structural formula:

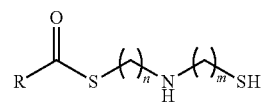

wherein
n is 2 or 3;
m is 2 or 3;
and RC(O)— is an amino acyl or peptidyl group, or R is selected from the group consisting of hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$.

25. The method of claim 24, wherein the method is conducted at a pH of between 4 and 6.

26. The method of claim 24, wherein the method comprises the step of applying microwave radiation.

* * * * *